(12) United States Patent
Korpela et al.

(10) Patent No.: US 8,430,247 B2
(45) Date of Patent: *Apr. 30, 2013

(54) METHOD AND A DEVICE FOR TREATING MICROPARTICLES

(75) Inventors: Matti Korpela, Naantali (FI); Kenneth Rundt, Turku (FI)

(73) Assignee: BioControl Systems, Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/300,347

(22) Filed: Nov. 18, 2011

(65) Prior Publication Data
US 2012/0128550 A1 May 24, 2012

Related U.S. Application Data

(62) Division of application No. 10/576,297, filed as application No. PCT/IB2004/003433 on Oct. 20, 2004, now Pat. No. 8,084,271.

(30) Foreign Application Priority Data

Oct. 20, 2003 (FI) ...................................... 20031535
Feb. 2, 2004 (FI) ...................................... 20040159

(51) Int. Cl.
*B03C 1/00* (2006.01)
*H01F 7/04* (2006.01)

(52) U.S. Cl.
USPC .......... 209/217; 209/216; 209/215; 209/219; 209/220; 209/221; 209/223.2; 209/224; 422/527; 422/549; 422/560; 210/222; 335/295; 335/302

(58) Field of Classification Search .......... 422/500–501, 422/527, 549, 560, 401, 409; 209/213, 215, 209/217, 219, 221, 223.2, 224; 210/222; 335/295, 302

See application file for complete search history.

(56) References Cited

U.S. PATENT DOCUMENTS

| | | | |
|---|---|---|---|
| 2,517,325 | A | 8/1950 | Lamb |
| 2,970,002 | A | 1/1961 | Laviano |
| 3,985,649 | A | 10/1976 | Eddelman |
| 4,041,764 | A | 8/1977 | Sabloewski et al. |
| 4,272,510 | A | 6/1981 | Smith et al. |
| 4,649,116 | A | 3/1987 | Daty et al. |
| 4,751,053 | A | 6/1988 | Dodin et al. |
| 5,183,638 | A | 2/1993 | Wakatake |
| 5,288,119 | A | 2/1994 | Crawford, Jr. et al. |
| 5,567,326 | A | 10/1996 | Ekenberg et al. |
| 5,837,144 | A | 11/1998 | Bienhaus et al. |
| 5,942,124 | A | 8/1999 | Tuunanen |
| 5,945,901 | A * | 8/1999 | Coleman et al. ............... 335/285 |
| 6,020,211 | A | 2/2000 | Tuunanen |
| 6,040,192 | A | 3/2000 | Tuunanen |

(Continued)

FOREIGN PATENT DOCUMENTS

| | | |
|---|---|---|
| DE | 100 57 396 C1 | 4/2002 |
| EP | 0 842 704 A1 | 5/1998 |

(Continued)

*Primary Examiner* — Brian R Gordon

(57) ABSTRACT

Method for handling microparticles in such a manner, that at least two treatment steps are performed for microparticles in the same vessel without moving the particles to another vessel. There are organs in the device for changing the solution without having to move the microparticles to another vessel.

9 Claims, 20 Drawing Sheets

U.S. PATENT DOCUMENTS

| | | | |
|---|---|---|---|
| 6,065,605 A | 5/2000 | Korpela et al. | |
| 6,187,270 B1 | 2/2001 | Schmitt et al. | |
| 6,207,463 B1 * | 3/2001 | Tuunanen | 436/526 |
| 6,403,038 B1 | 6/2002 | Heermann | |
| 6,448,092 B1 | 9/2002 | Tuunanen | |
| 6,468,810 B1 | 10/2002 | Korpela | |
| 6,596,165 B2 | 7/2003 | Koivula | |
| 6,648,810 B1 | 11/2003 | Tenerz et al. | |
| 6,649,419 B1 | 11/2003 | Anderson | |
| 6,666,978 B2 * | 12/2003 | Steinel | 210/808 |
| 6,764,859 B1 | 7/2004 | Kreuwel et al. | |
| 7,037,470 B2 | 5/2006 | Hardman et al. | |
| 7,220,385 B2 | 5/2007 | Blecka et al. | |
| 7,622,046 B2 * | 11/2009 | Rundt et al. | 210/695 |
| 7,632,405 B2 | 12/2009 | Siddiqi | |
| 7,632,462 B2 | 12/2009 | Holtlund et al. | |
| 7,648,844 B2 | 1/2010 | Srivastava et al. | |
| 2001/0020588 A1 | 9/2001 | Adourian et al. | |
| 2001/0022948 A1 | 9/2001 | Tuunanen | |
| 2004/0047765 A1 | 3/2004 | Gordon et al. | |
| 2006/0118494 A1 | 6/2006 | Rundt et al. | |
| 2006/0207944 A1 | 9/2006 | Siddiqi | |
| 2010/0126286 A1 | 5/2010 | Self et al. | |
| 2010/0159487 A1 | 6/2010 | Holtlund et al. | |

FOREIGN PATENT DOCUMENTS

| | | |
|---|---|---|
| EP | 0 787 296 B1 | 3/2001 |
| EP | 1 058 851 B1 | 7/2005 |
| WO | WO 87/05536 | 9/1987 |
| WO | WO 96/26011 | 8/1996 |
| WO | WO 01/51110 A1 | 7/2001 |
| WO | WO 01/60967 | 8/2001 |

* cited by examiner

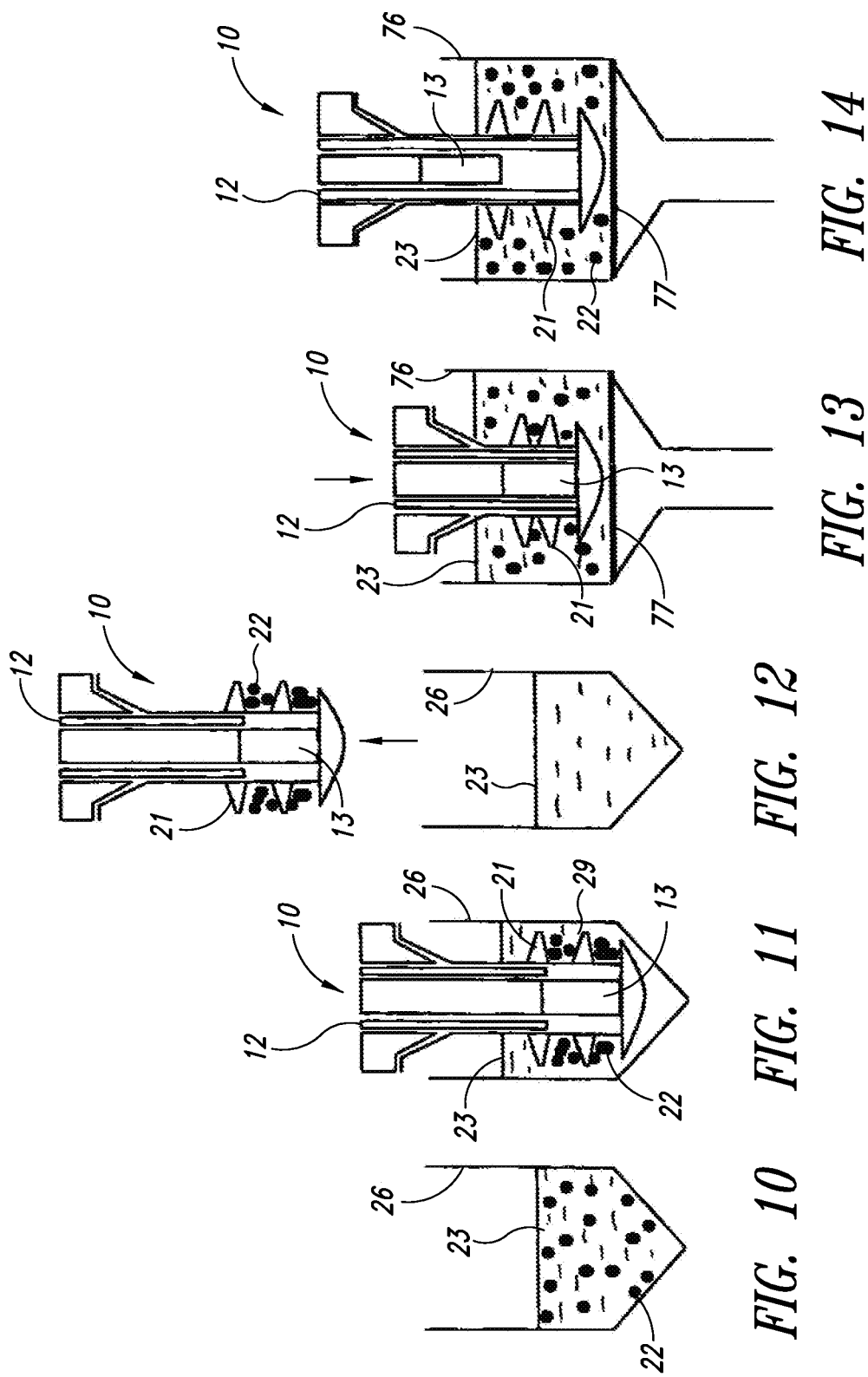

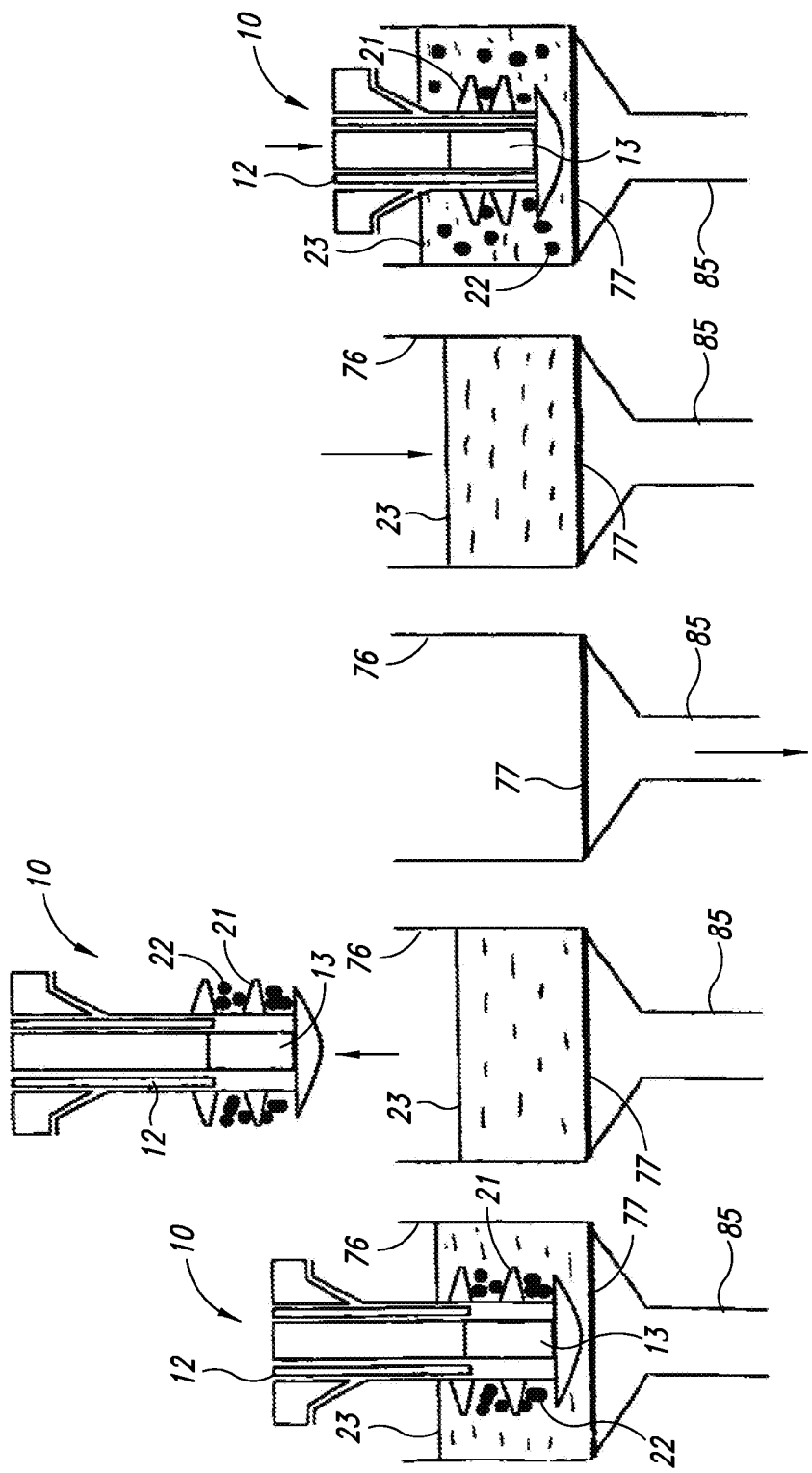

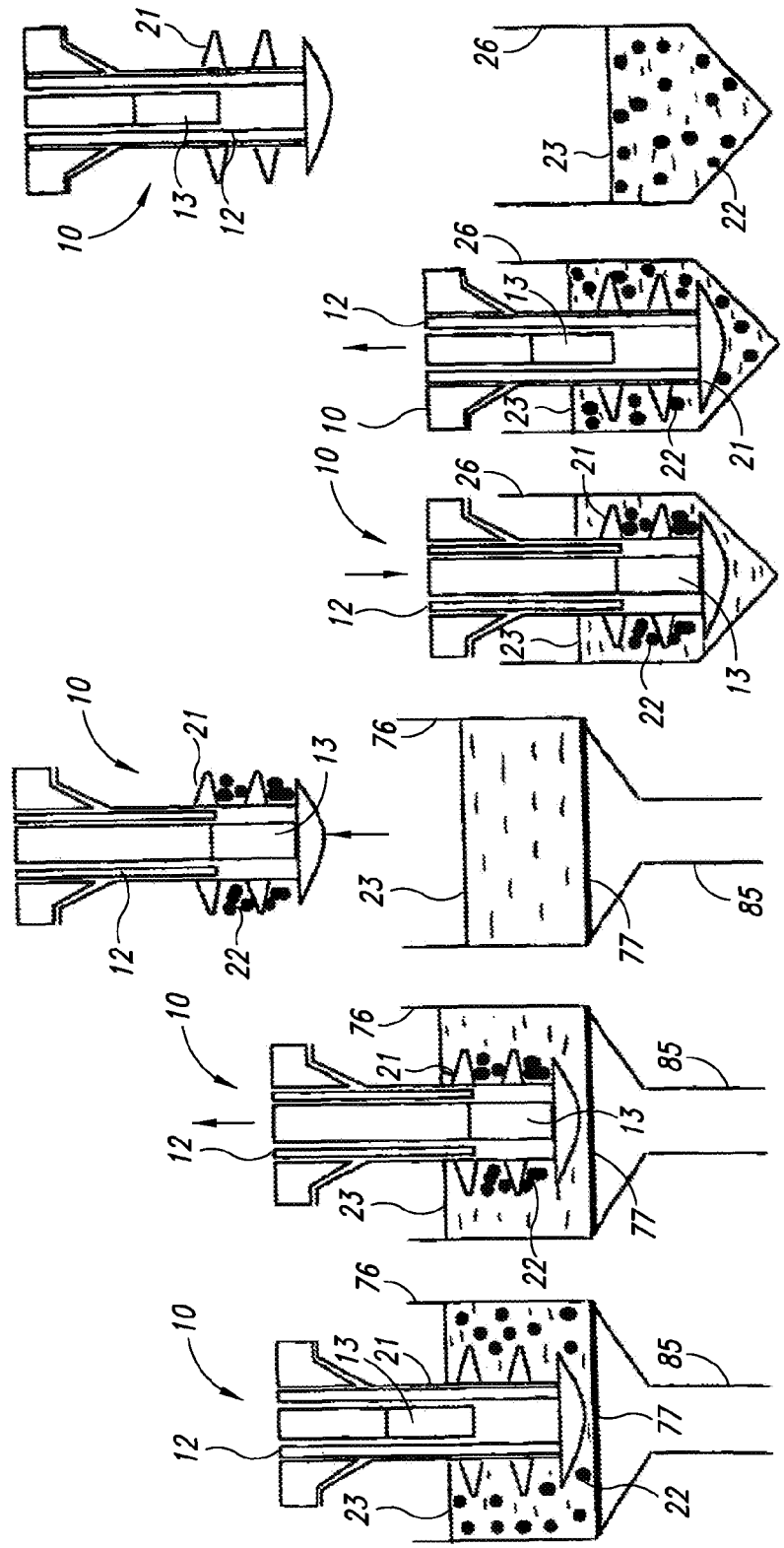

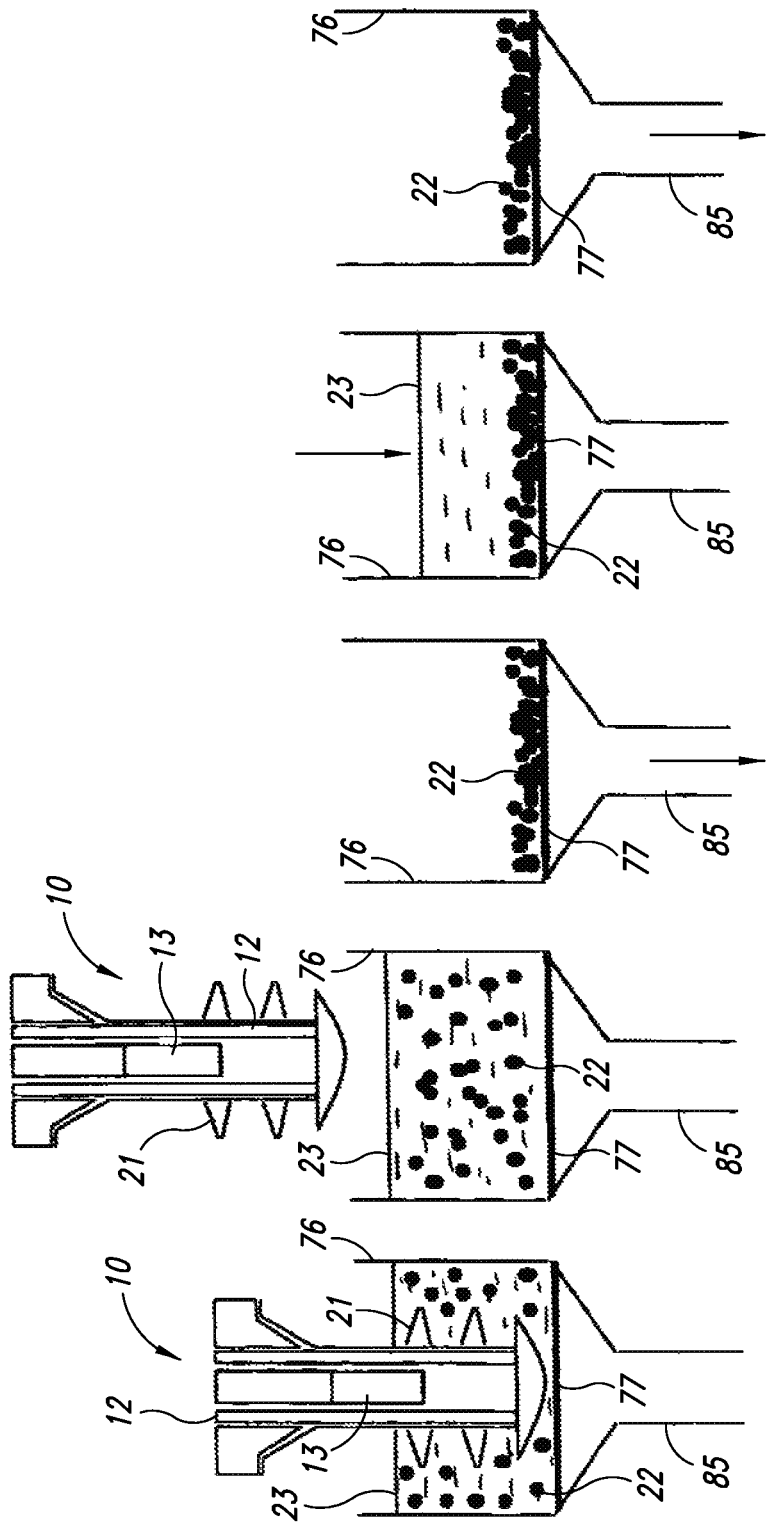

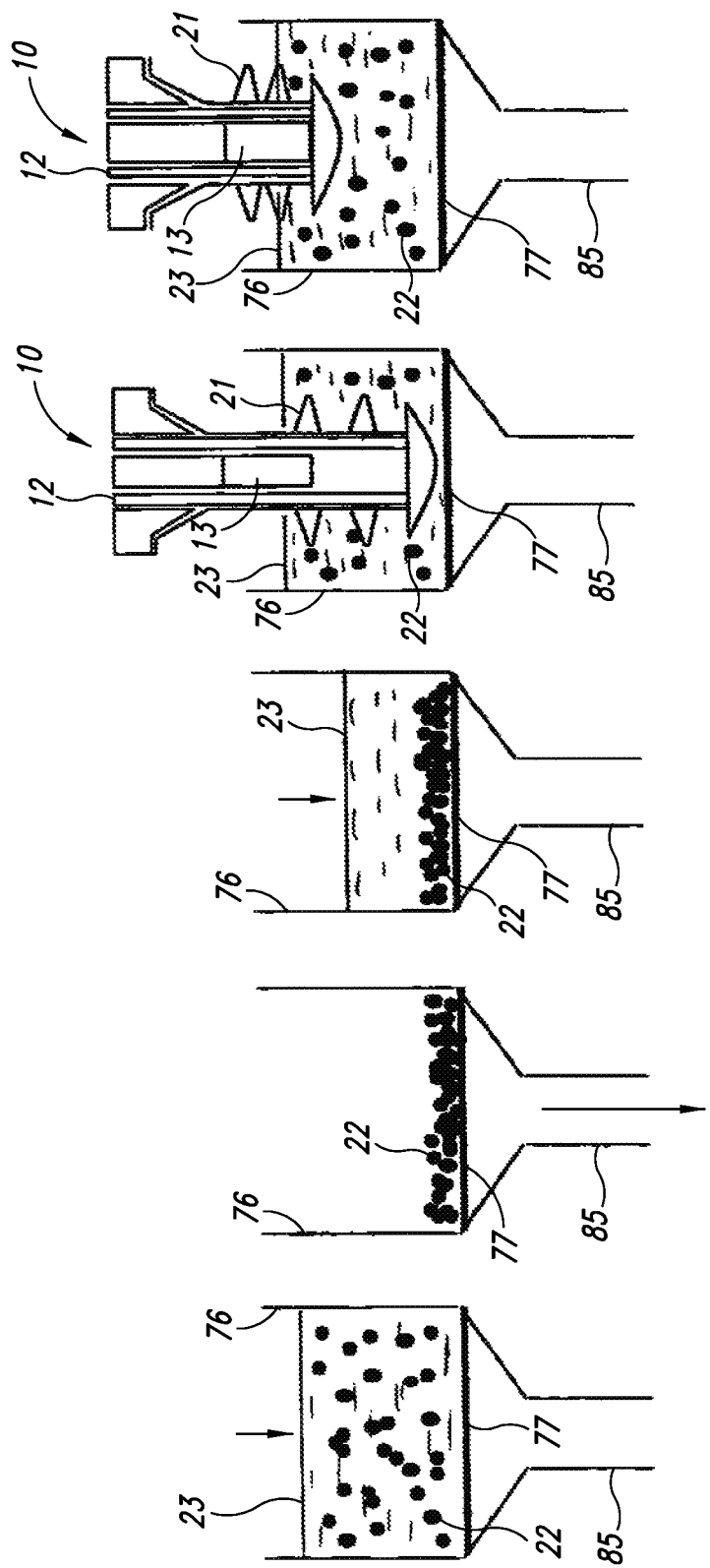

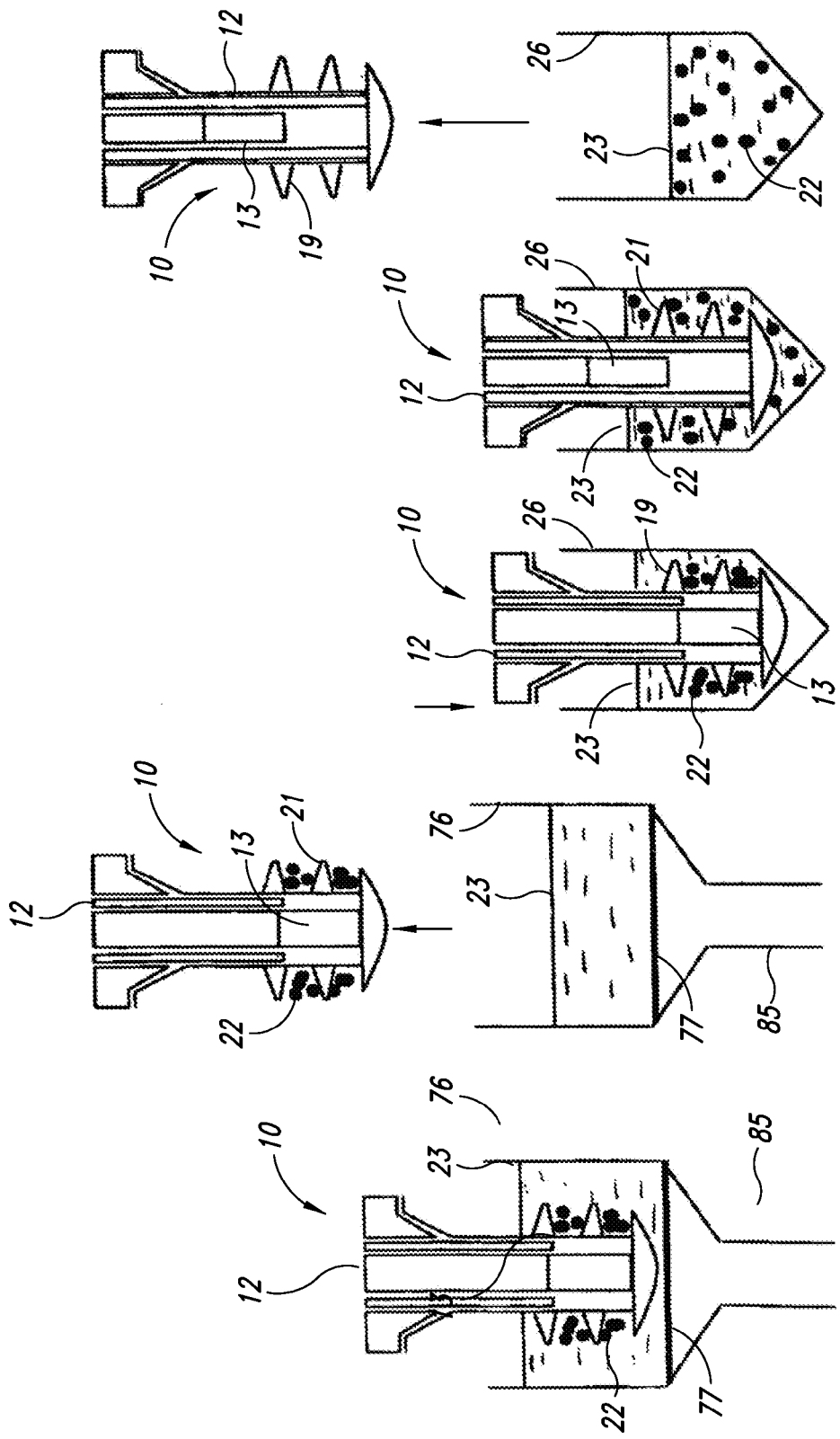

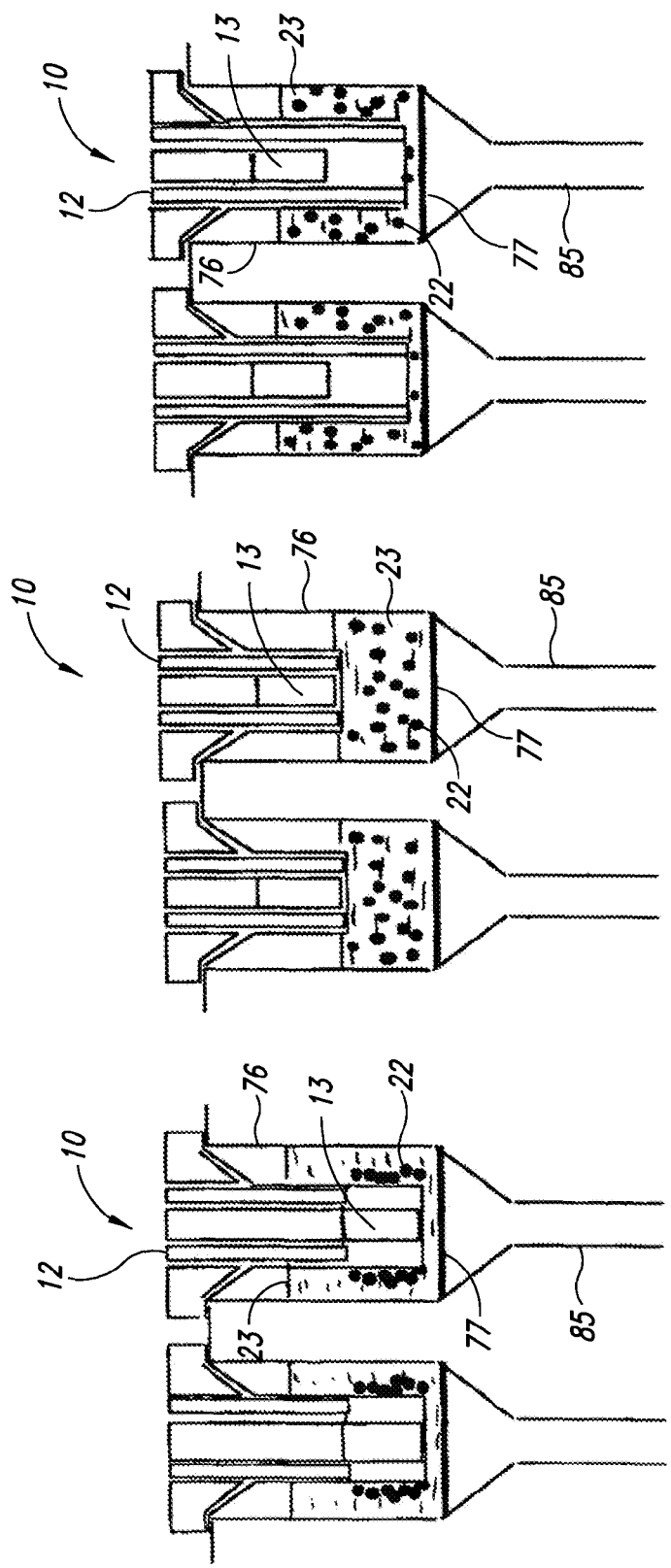

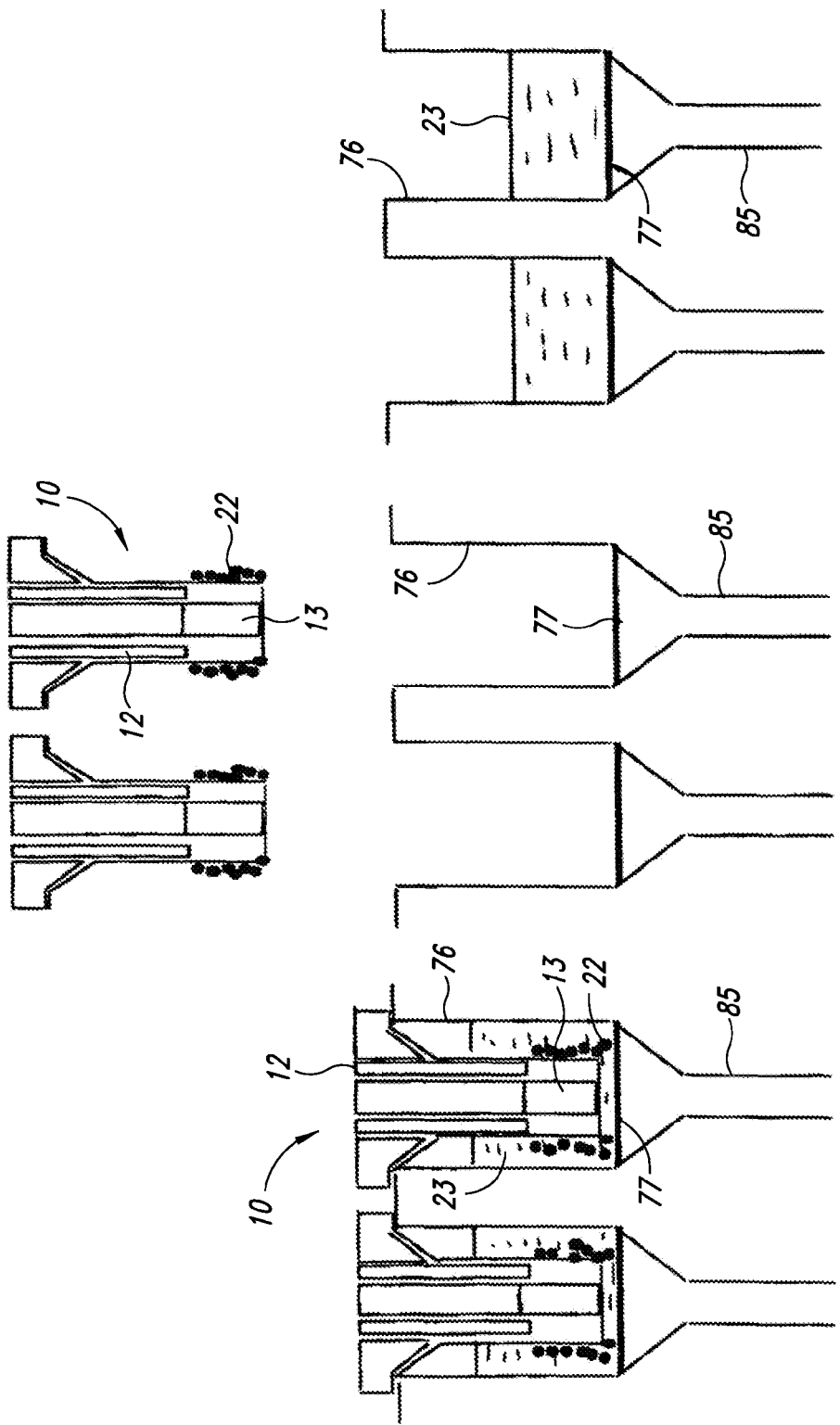

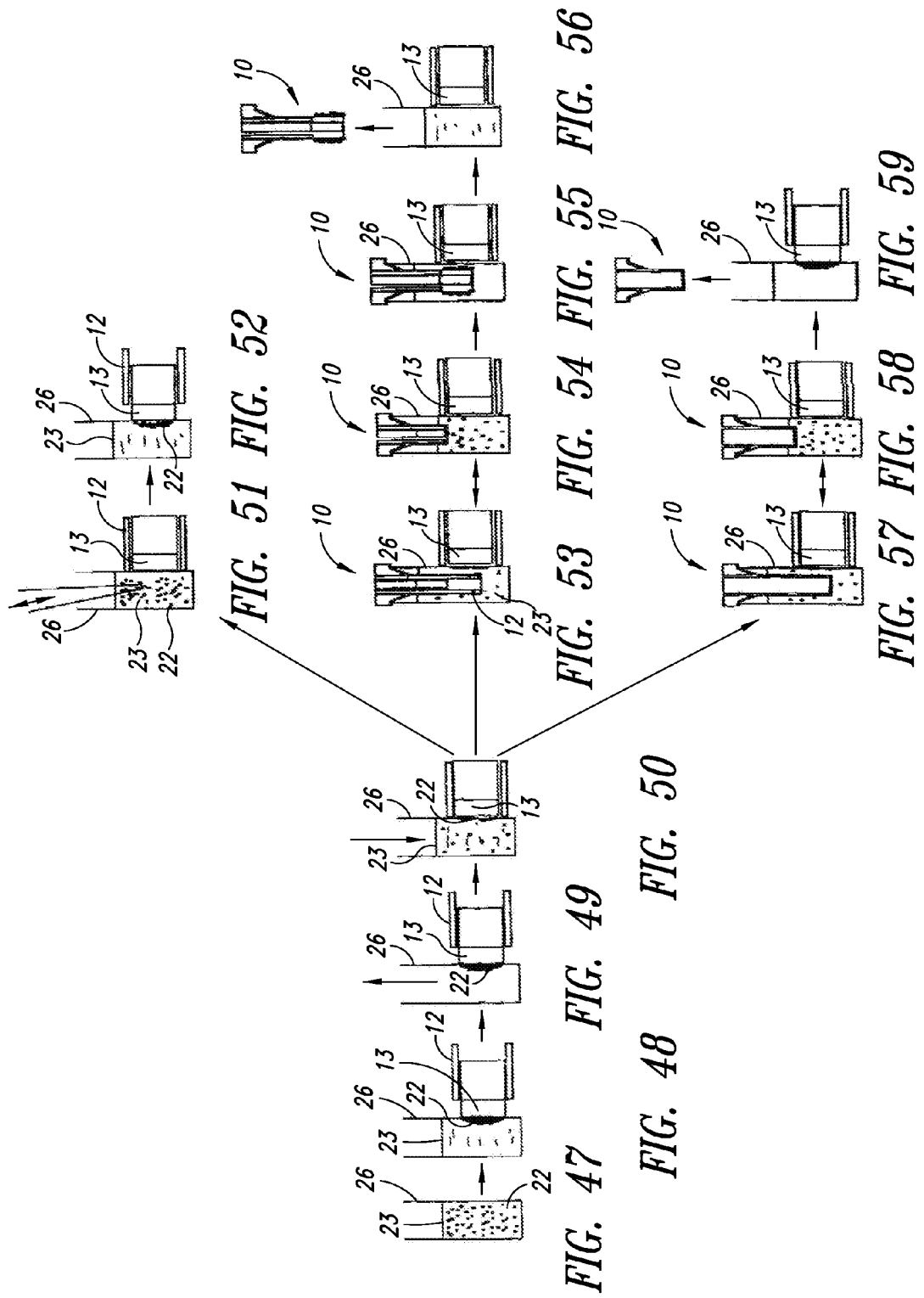

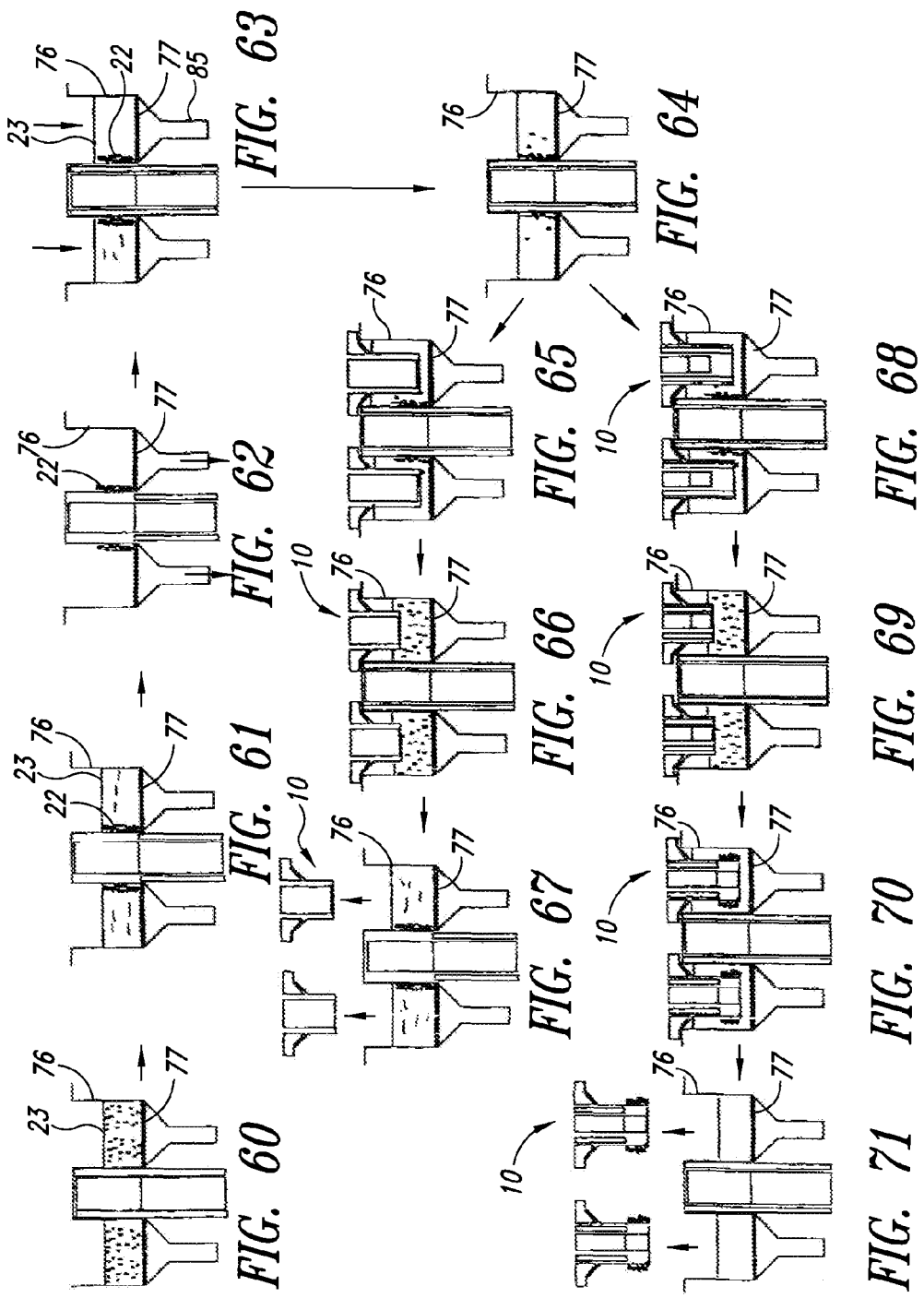

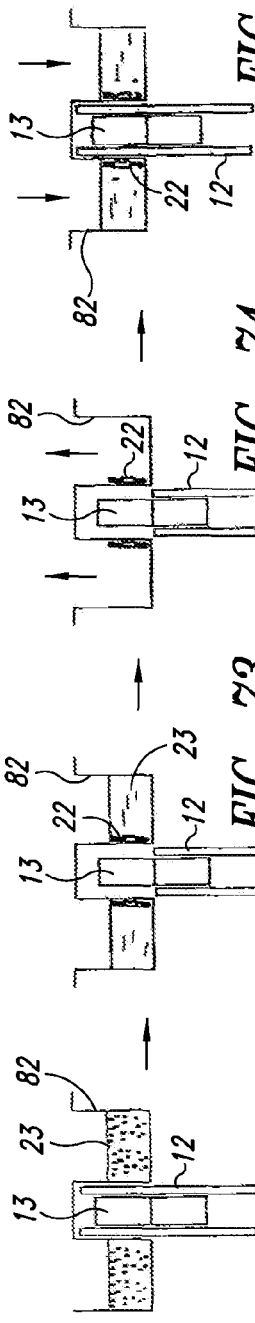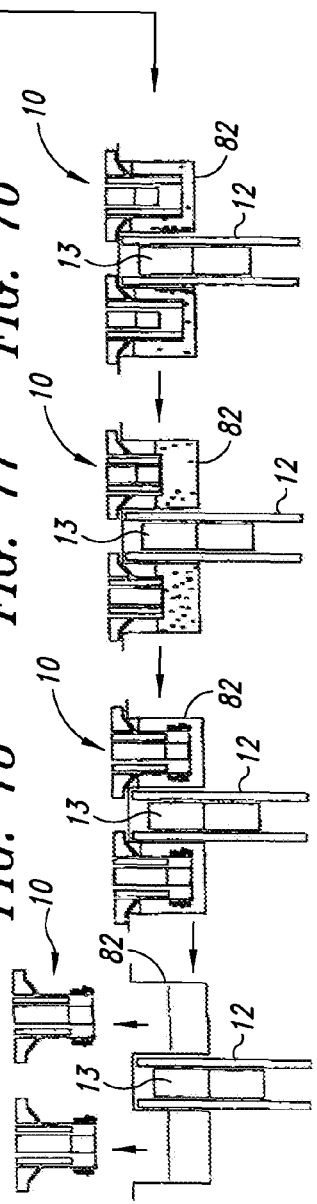

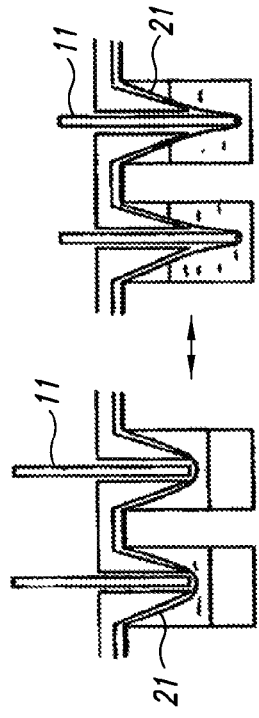
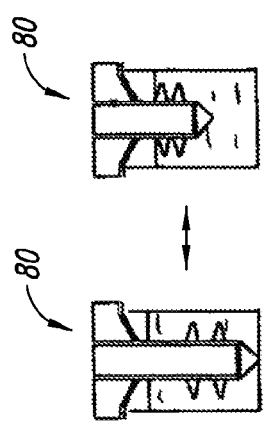
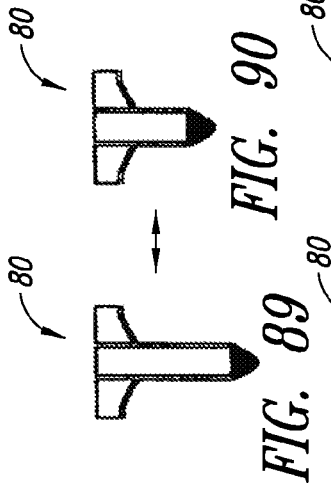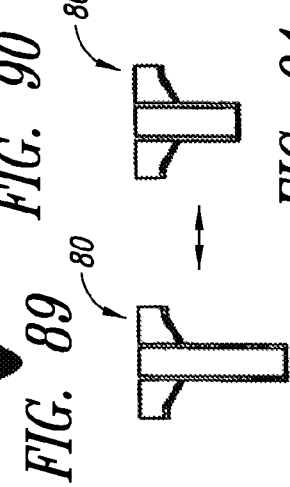
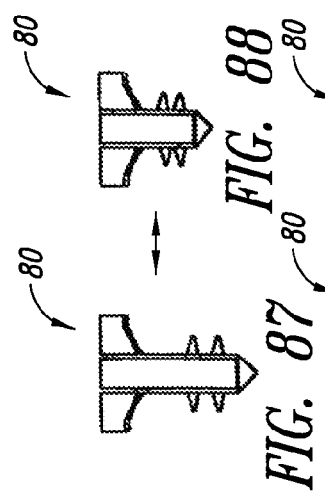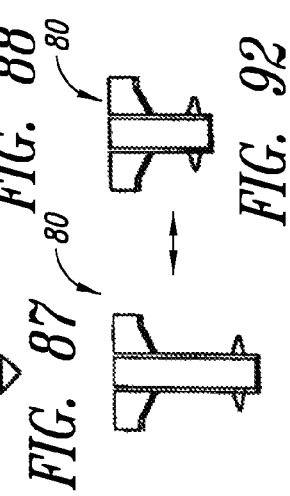

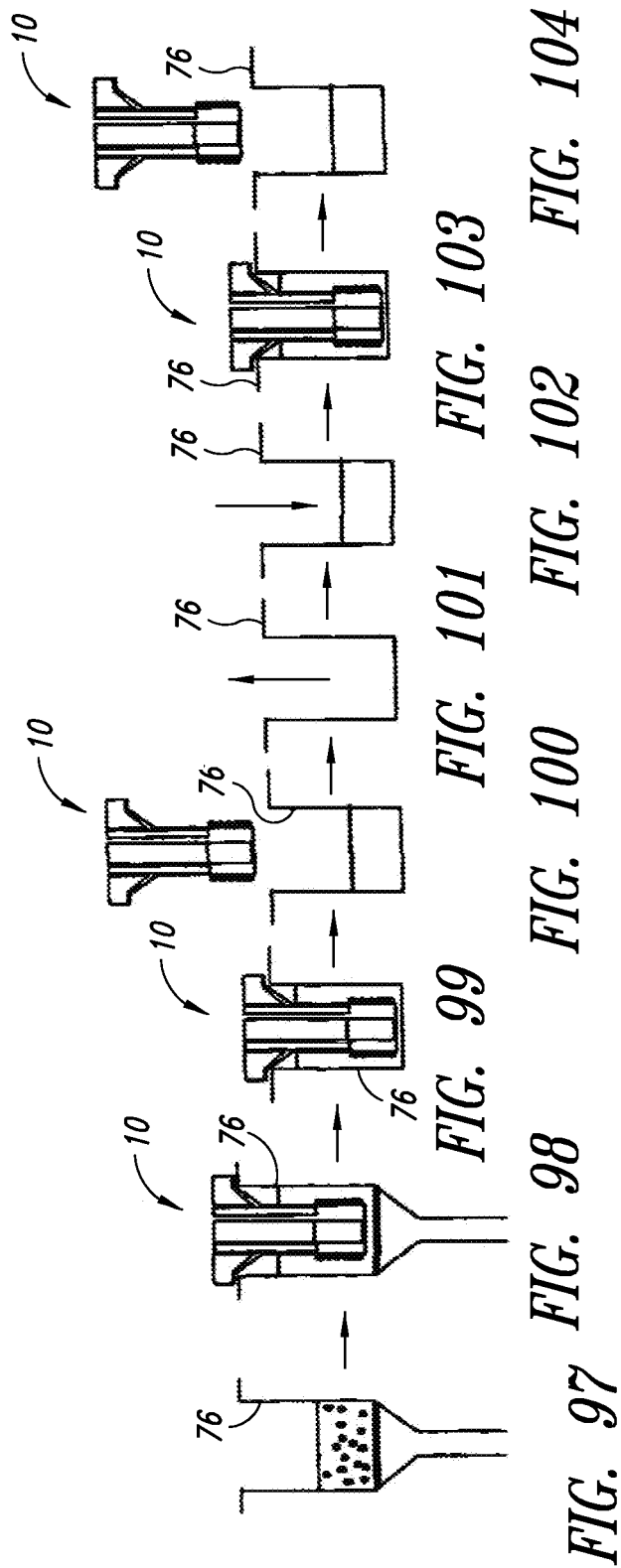

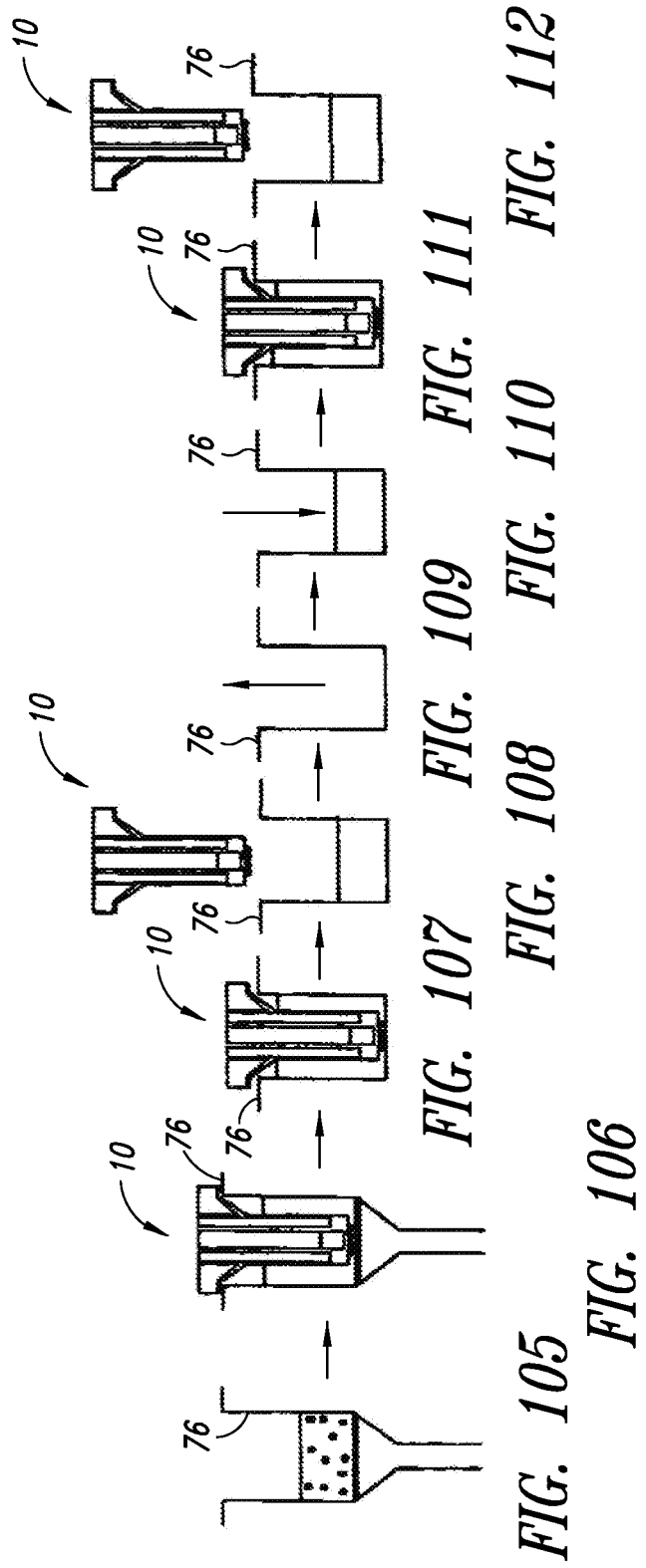

US 8,430,247 B2

METHOD AND A DEVICE FOR TREATING MICROPARTICLES

CROSS-REFERENCES TO RELATED APPLICATIONS

This application is a divisional application of U.S. application Ser. No. 10/576,297, filed Mar. 8, 2007, issued as U.S. Pat. No. 8,084,271; which application is a U.S. national stage application filed under 35 U.S.C. sctn. 371 of International Patent Application No. PCT/IB2004/003433, accorded an international filing date of Oct. 20, 2004, which application claims priority to Finnish Patent Application Nos. FI-20040159, filed Feb. 2, 2004, and FI-20031535, filed Oct. 20, 2003, which applications are incorporated herein by reference their entireties.

FIELD OF THE INVENTION

The invention relates to a method for treating microparticles. The invention further relates to a device for treating microparticles.

BACKGROUND OF THE INVENTION

Magnetic transfer method refers to all action related to the movement of particles by means of magnetism, such as assorting, collecting, transferring, mixing and dosing within a solution or from one solution to another.

Particles, microparticles or magnetic particles refer to all such small particles that have their diameter in the range of micrometers, and that can be moved by means of magnetism. There are various known particles that are transferable with a magnet and applications, where they are used, also greatly vary. For example, particles used in microbiology usually have a size of 0.01-100 µm, most commonly 0.05-10 µm. Such known particles are, for example, particles containing ferromagnetic, paramagnetic or supramagnetic material. Particles can also be magnetic themselves, whereby they can be moved by means of any ferromagnetic object.

In a device intended to treat microparticles, there is a unit exploiting magnetism, that is hereinafter referred to as a magnet. It can be a permanent magnet or an electrical magnet, that attracts ferromagnetic particles, or a ferromagnetic object, that is not magnetic itself, but still attracts magnetic particles.

A magnet is usually preferably a rounded bar magnet. It can also be a bar of another shape. However, a magnet does not need to be a bar at all. It can also be short and broad or an object of any shape. A magnet can also consist of one or more objects, such as magnets or ferromagnetic objects.

There has to be a shield covering the magnet, protecting the magnet from various harmful conditions and enabling the treatment of microparticles, such as binding and release. The structure of the shield may greatly vary, for it can be, for example, a thin membrane made of flexible or stretching material or even a cup made of rigid plastic.

Microparticles are usually used as the solid phase to bind various biomolecules, cell organelles, bacteria or cells. For example, enzymes can be immobilised on the surface of microparticles, whereby the treatment and further use of the enzymes is efficient. Most of the so called magnetic nanoparticles (<50 nm) are not suitable to be treated with regular permanent magnets or electrical magnets, but require the use of an particularly strong magnetic gradient, as described in EP 0842704 (Miltenyi Biotec). Magnetic particles, such as microparticles, that have a diameter of about 0.1 pm or more, can usually be treated with regular permanent or electrical magnets. The viscosity of the solution can also considerably hamper the picking of the particles. The particles to be picked can be originally suspended in the solution, where a substance is desired to be bound, or, say, cells on the surface of the microparticles.

PRIOR ART

Microparticles treated by means of a magnet have been used since the 1970's. This technique became very popular in immunoassays, among others. The use of microparticles in immunoassays to separate the bound antigen-antibody complex from the free fraction provided a considerable advantage particularly in the reaction rate. The main development concerning the use exploitation of microparticles has over the past years occurred in the field of molecular biology, microbiology and cell biology.

In a classical method the magnetic particles present in the reaction solution, such as microparticles, are captured by means of an external magnet to a given spot on the inner surface of the tube. Thereafter an effort is made to carefully remove the solution around the microparticles. In a classical method liquids are actively treated and magnetic particles stay in the same vessel during the whole procedure.

In another approach a magnet is used to actively transfer microparticles. The magnet is put in a solution containing microparticles, whereby the magnet attracts microparticles in the solution and they form a solid precipitate. Thereafter the magnet and the microparticles can be drawn out of the liquid. The magnet together with its particles can thereafter be soaked in a liquid in another test tube, wherein the microparticles can be released from the magnet. In this method the treating, pipetting and aspiration phases are minimised to the extreme.

U.S. Pat. No. 2,517,325 (Lamb) describes a solution for picking metal objects by means of a magnet. The publication describes a long bar magnet, that is moved inside an iron tube. The poles of the bar magnet are at the opposite ends of the longitudinal axis of the physical magnet. By moving the magnet out of the iron tube, the magnetic field becomes stronger. The publication describes a solution, wherein metal objects can be collected to the tip of the magnet unit. The publication also describes a solid plastic shield for protecting the magnet.

U.S. Pat. No. 2,970,002 (Laviano) describes a solution for collecting metal objects in liquids by means of a magnet. The publication describes a long permanent magnet, that collects particles to the tip of the magnet unit. The magnet is attached to the metal bar and protected with a separate plastic shield. The publication describes the simultaneous use of moving of the permanent magnet and the plastic shield used to protect the magnet. The publication describes the collecting of metal objects to the tip of the magnet unit and the release of the metal objects from the top of the shield by means of a particular design of the plastic shield.

U.S. Pat. No. 3,985,649 (Eddelman), U.S. Pat. No. 4,272,510 (Smith et al.), U.S. Pat. No. 4,649,116 (Daty et al.), U.S. Pat. No. 4,751,053 (Dodin et al.) and U.S. Pat. No. 5,567,326 (Ekenberg et al.) describe solutions, wherein magnetisable material is collected directly from the solution with a magnet in each of them. It is also common for these publications that the magnets are not protected with separate plastic shields. These solutions also require washing of the tip of the magnet before treating the next sample to eliminate the risk of contamination and the carry-over effect of impurities.

U.S. Pat. No. 5,288,119 (Crawford, Jr. et al.) describes a solution, wherein metal objects can be collected by means of a magnet. The magnet of the device according to the publication is not protected with a particular shield and it is not suitable for picking metal objects in liquids. The publication describes a solution for picking larger metal objects. The publication shows a long bar magnet, that is moved inside a non-magnetic tube. A special characteristic of this tube is that it acts as a blocking of the magnetic field, although it is not magnetic. As alternative materials for this purpose the publication shows, for example, bismuth or lead or a mixture thereof. The magnet of the device according to the solution is not protected with a particular shield and it is not suitable for picking metal objects in liquids.

WO Application 87/05536 (Schröder) describes the use of a permanent magnet, movable inside the plastic shield, for picking ferromagnetic material in a solution containing them. Ferromagnetic material gathers to the tip of the magnet unit, while the magnet is in its lower position. The publication describes the transfer of the ferromagnetic material collected in this manner into a solution in another vessel and the release of the material there off the tip. The release of the ferromagnetic material is described by means of the design of the plastic shield that prevents the material from moving while moving the magnet upwards.

U.S. Pat. No. 5,837,144 (Bienhaus et al.) describes a method for collecting microparticles by means of a magnet equipped with a particular plastic shield. This publication describes the binding of microparticles in a solution, which is conducted out of the vessel by different arrangements. By moving the magnet the microparticles can be made to become free from the surface of the protective shield.

U.S. Pat. No. 5,942,124 (Tuunanen), U.S. Pat. No. 6,020,211 (Tuunanen), U.S. Pat. No. 6,040,192 (Tuunanen), U.S. Pat. No. 6,065,605 (Korpela et al.), U.S. Pat. No. 6,207,463 (Tuunanen) and US Patent Application 20010022948 (Tuunanen) also describe devices equipped with a plastic shield for collecting microparticles in a solution and transferring them to another solution. These publications primarily describe solutions, where the intention is to treat microparticles in very little volumes. U.S. Pat. No. 5,942,124 (Tuunanen) describes a device, by means of which microparticles can be enriched right to the tip of the magnet unit. U.S. Pat. No. 6,020,211 (Tuunanen) describes the use of the device presented in the previous publication for transferring microparticles collected together by means of a big, so called classical magnet to smaller vessels. U.S. Pat. No. 6,040,192 (Tuunanen) describes an automated method for using microparticles in specific assays and for handling small volumes. U.S. Pat. No. 6,065,605 (Korpela et al.) continues to further apply the solution described in U.S. Pat. No. 5,942,124 (Tuunanen) for handling fairly large volumes. Now a method, whereby microparticles have first been collected by means of a particular magnet unit containing a big magnet, is described. Thereafter the magnet unit described in U.S. Pat. No. 5,942,124 (Tuunanen) is used for transferring the pellet of microparticles further into smaller vessels. U.S. Pat. No. 6,207,463 (Tuunanen) also applies the previously described magnet unit, by means of which magnetic particles can be collected right to the tip of the device. US Patent Application 20010022948 (Tuunanen) describes also the treating of a very small amount of microparticles in particular vessels design for this purpose.

U.S. Pat. No. 5,942,124 (Tuunanen), U.S. Pat. No. 6,020,211 (Tuunanen), U.S. Pat. No. 6,065,605 (Korpela et al.), U.S. Pat. No. 6,207,463 (Tuunanen) and EP 0 787 296 (Tuunanen) describe a method, where a large amount of microparticles are intended to be collected from a fairly large vessel by means of a very small magnet to the small tip of a very sharp and narrow bar, the method being impractical.

U.S. Pat. No. 6,403,038 (Heermann) describes a device, that has a plastic shield and a permanent magnet attached to a particular bar. Microparticles are collected to the tip of the plastic shield and the method is particularly intended for treating small volumes. The bar has a particular, projecting part, by means of which the magnet and the bar keep still in the protective tube.

EP Patent 1058851 (Korpela) and Patent Application WO 01/60967 (Korpela) describe devices, that have a stretchy, elastomeric protective membrane. In these solutions the microparticles are collected on the surface of the stretchy protective membrane, where they can be further transferred to another vessel. The protective shield of the magnet is made of stretchy material, whereby the membrane is as thin as possible when stretched. In this way a distance as small as possible from the magnet to the liquid is brought about.

Currently known approaches require either transferring the microparticles from one vessel to another containing a new solution or binding the microparticles to the inner surface of the vessel while removing the previous solution and replacing it with a new one. The previous manner consumes a lot of vessels, because each new wash or incubation requires the use of a new vessel. In this method the use of disposable vessels is extensive and also the solutions concerning devices require developing of a large device. The latter manner i.e. the so called conventional manner to treat microparticles has the problem of controlling the magnetic field to be used and homogenisation of the microparticles. The normal manner, for example, using 96-well plates, is to use a magnet plate, that has either magnet pivots or magnet bars on top of the plate. The magnets on the magnet plate are placed in such a manner that they go into the spaces and gaps between the wells of the 96-well plate to be used. While the 96-well plate is placed on top of such a magnet plate, the magnets bring about a magnetic field in the wells of the 96-well plate and the microparticles in these wells attach to the inner surface of the well to form a layer of microparticles. Now the solution may be removed from the well, for example, by means of a pipette and the next solution may be brought in. The microparticles need to be homogenised in the solution off the inner surface of the well and for this purpose the 96-well plate needs to be removed from its position on top of the magnet plate in order to disconnect the magnetic field. Homogenisation of the microparticles in the solution, mixing the solution and the microparticles in the well as well as evaporation of the liquid are problems, not easy to solve, in the conventional method. These problems are particularly pronounced in small vessels, such as, for example, when using 96-, 384- and 1536-well plates.

According to one preferred embodiment the microparticles are bound on the surface of a specific magnetic device and the solutions may be changed through a hole on the bottom of the vessel. In this particular method, though, neither transferring of microparticles from one vessel to another, removing the microparticles temporarily away from the vessel while changing the solutions, mixing the solution and/or the microparticles nor closing the vessel, is being solved.

None of the previously described publications describe a method, by means of which microparticles could be efficiently collected, mixed and incubated particularly in small volumes. Neither do the publications describe an efficient manner to transfer microparticles within one vessel, to transfer microparticles from the vessel nor to change solutions when the need arises depending on the application.

Method

The purpose of this invention is to bring about such a method for treating microparticles that does not have the previously presented disadvantages. It is characteristic for the method according to the invention that at least two treatment steps are performed in the same vessel without moving the particles into another vessel.

The invention relates particularly to collecting microparticles, removing and adding solutions in one vessel, mixing microparticles in the vessel, closing the opening of the vessel and transferring microparticles from one solution to another. By means of the method according to the invention, operation of a large sample volume by means of a vessel including a filter and coating of the magnet unit or its protective membrane with microparticles, may be performed. A coating, brought about in such a manner, may be used in, for example, purifications and immunoassays.

The method may be used particularly in automated devices, where various transfers, washes and incubations of microparticles may be performed. It is possible to join the automated device to units, whose purpose is, for example, to detect PCR reactions and/or various labels used in immunoassays.

Device

It is characteristic for a device for treating microparticles that there are organs in the device for changing the solution in such a manner, that at least two treatment steps for the microparticles can be done in the same vessel without transferring the particles to another vessel.

The invention further relates to a device for mixing microparticles, closing of the opening of the vessel to be used, a specific mixing device, operating a large sample volume by means of a vessel including a filter and a magnet unit as well as its protective membrane.

The crucial property of the wash station for microparticles according to the invention is that the microparticles do not need to be transferred to another vessel, but various incubations and washes may be performed in the same vessel. The solution may be changed in the vessel by, for example, aspirating the solution away from the vessel through a filter on the bottom of the vessel or a specific channel. Aspirating the solution may be performed, for example, by means of an aspiration or vacuum device, that is joined to the vessel to be treated. Alternatively, aspiration of the solution from the vessel may be performed by means of a pipette or a washing device. Microparticles are bound on top of the protective membrane of the magnet unit or on the inner surface of the vessel to be used by means of an external magnet and a ferromagnetic sleeve, while changing the solutions. The new solution may be brought into the vessel by pipetting or by means of various dispensers/washers. One of the advantages of the wash station for microparticles according to the invention is that microparticles do not always need to be transferred to new vessels, while new solutions are being introduced. In this way a lot of disposable plastic ware, such as, for example, plates and tubes, can be saved and the size of the automated devices may be elaborated to become remarkably small. It is particularly easy to disconnect and connect the magnetic field, when using the wash station according to the invention.

One wash station according to the invention may be realised by means of an external magnet and a ferromagnetic sleeve/plate. In this case the ferromagnetic sleeve is used in an appropriate manner to remove or create the magnetic field in the vessel. Removing the solution from the vessel may be brought about by either aspirating the solution through a filter/membrane/channel on the bottom of the vessel or by means of a pipette/washing device from the top of the vessel. Microparticles are collected before removing the solutions either on the inner surface of the vessel to form a layer or on top of the protective membrane of the magnet unit. The next solution may be brought in by means of a pipette or a dispenser/washer. In one embodiment of the invention, a specific mixing tool is brought into the vessel, which tool consists of a bar inside of a protective membrane consisting of elastomer material, which bar may be used to stretch or loosen the protective membrane. In this way an efficient mixing is brought about in the solution inside the vessel. Mixing can also be arranged by means of the protective membrane of the magnet unit, whereupon the movement of the magnet and the ferromagnetic sleeve inside the protective membrane in relation to each other is exploited.

An external magnet and ferromagnetic sleeve/aperture plate may act together with the vessel in such a manner, that there is an appropriate spring under/on one side of the magnet. While resting, me magnet is situated outside the ferromagnetic sleeve/aperture plate by means of the spring and a magnetic field is directed towards the vessel. While pushing the magnet inside the ferromagnetic field, the spring yields and there is no magnetic field directing to the vessel. A specific locking mechanism may be arranged in the wash station in order to keep the spring yielded. It is possible to replace the spring with a specific motorised solution, whereupon the magnet is moved under controllable conditions in relation to the ferromagnetic sleeve.

The opening of the vessel may be tightly closed by means of a magnet unit used together with a wash station according to the invention, for example, during the incubations. This property is of great importance when using small volumes of solution, whereupon evaporation of the solution is often a considerable problem. Also incubations at high temperatures and long incubation times require closing of the vessels during the incubations. By means of tools according to the invention, solutions and/or microparticles can be mixed, while the vessel is closed without the help of an external mixer/shaker. In the mixing manner according to the invention, by stretching and loosening the protective membrane consisting of elastomer material, an efficient mixing may be brought about in even small vessels. The protective membrane may have appropriate forms to enhance the mixing efficacy.

Microparticles may be brought to form a layer of microparticles on the surface of a filter or a membrane by means of the method according to the invention. By means of such a method application of microparticles, for example, a large sample volume may be aspirated through the layer of microparticles and the filter under it. The microparticles in the layer of microparticles may be coated, for example, with specific antibodies, to which the desired components in the sample are bound. Thereafter the microparticles may be collected from the layer onto the surface of the protective membrane by means of the magnet unit and transferred from the vessel including the filter. The components collected from the sample may be released to an appropriate solution off the surface of the microparticles or the microparticles may be processed further depending on the application in question.

In one method according to the invention the microparticles are bound to the protective membrane of the magnet unit to form a layer. The magnet unit and the solution containing the microparticles are mixed appropriately in order to make the layer on top of the protective membrane as homogenous and thin as possible. By using a transversely magnetised magnet a very large area of the surface of the protective membrane may be taken into use to collect microparticles to form a thin layer on top of the protective membrane. On the other hand, a magnet that is magnetised along the longitudinal axis of the magnet unit, which magnet collects microparticles to the very tip of the protective membrane, is a preferred alternative, when a very large solid-phase area is not needed for the assay/purification, but the desired volumes of solution are very small. A large amount of microparticles is not the most important circumstance in this solution, but the fact, how large the area and how homogenous the layer is, where the microparticles are arranged. A microparticle coating, brought about in such a manner, is particularly preferred to be used, for example, when performing an immunoassay. It is desired in immunoassays, as well as in many other analytical applications, that the collecting solid-phase is as large as possible, whereupon the sensitivity of the measurement may be increased and the reaction kinetics may be enhanced. In this case the microparticles are not to be released from the surface of the protective membrane, but all the incubations and washes are performed together with the layer of microparticles. It is also secured by means of this solution, that microparticles are not lost during the process compared to the case, where the microparticles are released in each wash step to the solution and gathered back from it after the wash step. Also in this case the wash station, mixing and closing of the opening of the vessel according to the invention may be utilised. In one embodiment all necessary solutions and microparticles may be readily dispensed beforehand in separate vessels and the vessels may also be closed. Such an approach is preferred, when a very simple and ready-to-use method is desired to be developed. In one embodiment according to the invention there is no separate shield or protective membrane around the magnet or the magnets in the magnet unit; but the magnet may be coated in appropriate manner, for example, with a phosphate, epoxy or nickel coating.

The magnet in the magnet unit according to a preferred embodiment of the invention has the essential technical characteristic, that the strength and the adjusting of the magnetic field can be regulated in relation to the protective membrane surrounding the magnet. This can be brought about by moving the magnet inside the ferromagnetic tube in such a manner, that it can be completely inside the tube, whereupon the efficiency of the magnet is insignificant or nonexistent, or it can be partially or completely outside the tube, whereupon the efficiency and the collecting area of the magnet are in relation to the protruding part of the magnet. Combining these characteristics for transferring magnetic particles to vessels of appropriate sizes a very efficient collecting and enrichment event is brought about.

A ferromagnetic tube can consist of iron or other suitable material, which has appropriate characteristics to stop the magnetic stream from getting through the tube. The efficiency of the magnet can be regulated by changing the place of the magnet in relation to the ferromagnetic tube in such a manner, that a part of the magnet is inside the tube. Alternatively the magnet can be kept still and the ferromagnetic tube is moved in relation to the magnet. The magnet is attached to a bar, that can be ferromagnetic or is not ferromagnetic, and by means of which the magnet can be moved in the ferromagnetic tube.

The magnet can have the shape of a round bar or a peg, but it can also have another shape. The magnetising axis of the magnet may also vary. The magnetising axis can be either longitudinal, whereupon it is parallel to the longitudinal axis of the bar and the poles of the magnet are at the ends of the bar. Then the magnetising is parallel to the ferromagnetic tube, i.e. parallel to the direction of movement of the magnet or the tube.

However, the magnetising axis of the magnet can also be transverse, whereupon it is perpendicular in relation to the longitudinal axis of both the ferromagnetic tube and the bar-like magnet. Then the direction of magnetisation is transverse to the direction of movement of the magnet or the tube.

On the other hand the magnet can also consist of several separate magnets, that can be alike or different and that can be attached to each. other by means of magnetic force or through a material, that is ferromagnetic or non-ferromagnetic. The magnet may also be a combination of magnetic and ferromagnetic material. The magnet may also be either a permanent magnet or an electrical magnet.

By means of the magnet arrangement, protective membrane and the vessels to be used, microparticles can be treated very efficiently in both large and small liquid volumes. Focusing the micoparticles to the very tip of the magnet unit enables both concentrating from large volumes and treating microparticles in small volumes. Indeed, a universal solution for applications including microparticles both on large and small scale is described in the invention.

The invention presents that by designing the form of the outer surface of the plastic shield or the elastomer in a particular manner sufficient support is achieved to collect the mass of microparticles to be collected around the shield in a preferable and reliable manner. The term particular design of form refers to, for example, grooves, cavities and/or protuberances of different sizes and depths. When gathering between these formations, the pellet of microparticles gets particular support from the shield, while the magnet unit is moved against liquid currents. The effect produced by viscose samples is very significant, which means at worst, that microparticles do not stay attached to one side of the shield, but stay in solution. The above-described form has naturally a great benefit to the collecting reliability, when handling large volumes.

The invention describes a magnet unit, by means of which microparticles may be collected in many different applications. The essential technical solution in the invention is the possibility to, by means of a ferromagnetic tube, regulate the force and the adjustment of the magnetic field to the surrounding protective membrane, around of which the microparticles are collected. The magnet can be moved in and out in relation to the ferromagnetic tube, whereupon the magnetic field of the magnet is changed. While the magnet is out, a magnetic field equal to the amount of magnet outside of the ferromagnetic tube is adjusted to the protective shield. Then microparticles can be collected outside of the protective shield. When the magnet is completely moved inside the ferromagnetic tube, there is no considerable magnetic field adjusting outwards. In this case the microparticles do not gather around the protective membrane, but stay in solution. The tube can be solid or adjustable in order to achieve the best possible efficiency for collecting. The magnet and the ferromagnetic tube/sleeve according to the invention are in use also in the extra-vessel solution, whereupon collecting of microparticles to the inner surface of the vessel is controlled by means of the magnet.

The microparticles may contain affinity ligands, enzymes, antibodies, bacteria, cells or cell organelles. Binding of the desired components can also be brought about by choosing the surface properties of the microparticles to be used and the composition of the buffers in an appropriate, preferable manner in order to bind the desired components from the samples.

Examples include ion exchange, hydrophobic and reverse phase chromatography. Then, for example, binding and releasing of proteins from the surface of the microparticles is performed by means of appropriately chosen buffers and solutions. For example, salt content and pH value are then very important factors.

An affinity ligand may be, for example, a one- or two-stranded nucleotide sequence, such as, for example, DNA (Deoxyribonucleic Acid), RNA, mRNA or cDNA (Complementary DNA) or PNA (Peptide Nucleic Acid), a protein, a peptide, a polysaccharide, an oligosaccharide, a small molecular compound or a lectin. An affinity ligand may also be one of the following: Ovomucoid, Protein A, Aminophenyl Boronic Acid, Procion Red, Phosphoryl Ethanolamine, Protein G, Phenyl Alanine, Proteamine, Pepstatin, Dextran sulfate, EDTA (Ethylenediaminetetraacetic Acid), PEG (Polyethylene Glycol), N-acetyl-glucosamine, Gelatin, Glutathione, Heparin, Iminodiacetic Acid, NTA (Nitrilotriacetic Acid), Lentil Lectin, Lysine, NAD (Nicotinamide Adenine Dinucleotide), Aminobenzamidine, Acriflavine, AMP, Aprotinin, Avidin, Straptavidin, Bovine Serum Albumin (BSA), Biotin, Concanavalin A (ConA) and Cibacron Blue.

Immobilising an enzyme or an affinity ligand means, that an enzyme or an affinity ligand is attached to the surface of the particles or that it is captured inside a "cage-like" particle, however in such a manner, that the surrounding solution gets in contact with it.

Attaching the enzyme or the affinity ligand to the microparticles can be done by means of a covalent binding, for example, by means of the amino and hydroxyl groups in the carrier. Alternatively the binding can be brought about by means of a bioaffinity pair, for example, a biotin/streptavidin pair. According to one way the enzyme to be immobilised is produced with DNA technology, for example, in *Escherichia coli* bacteria and a particular enzymatic tail has been prepared to the enzyme. This affinity tail binds to microparticles, to which a component, binding strongly to the affinity tail in question, is attached in an appropriate manner. The affinity tail may be a small molecular compound or a protein. With this arrangement microparticles could be efficiently utilised while purifying the desired enzyme and, at the same time, the enzyme bound to the microparticles would be readily immobilised on the surface of microparticles to be used in the method described in the invention.

Attaching of the enzyme or the affinity ligand may also be unspecific, non-covalent, such as adsorption.

The definition "microparticle" refers herein to particles that have a recommended size of 0.10-100 µm. A microparticle can also be a remarkably larger particle, for example, a particle that has a diameter of several millimeters. In the invention microparticles are magnetic, such as, for example, para-, superpara- or ferromagnetic, or consist of magnetisable material, or the microparticles are attached to a magnetic or magnetisable piece. Microparticles to which, for example, affinity ligands or enzymes may be attached, are captured in the vessel by means of a magnet unit soaked in the vessel, the microparticles are washed in the same vessel, the opening of the vessel may be closed, the solution and the microparticles may be mixed by stretching the protective membrane consisting of elastomer material, the magnet unit is possibly transferred to another vessel and the microparticles are released by the action of the magnet in various appropriate ways as described in the invention. Alternatively the microparticles do not need to be particularly liberated from the magnet unit.

The magnet by means of which the particles are captured, can either be a permanent magnet or an electrical magnet. The shape of the magnets may vary depending on the application. The magnetic field can be different in the magnets: a longitudinally magnetised magnet, a magnet magnetised along the diameter of the magnet or several magnetic poles in the same magnetic piece. Individual magnets may also be joined to each other by means of appropriate ferromagnetic or non-ferromagnetic spacers.

The protective membrane may consist of inelastic material, such as, for example, polypropylene, polystyrene, polycarbonate, polysulfone and polyethylene. The protective membrane may also consist of non-ferromagnetic metal or ferromagnetic metal. The protective membrane may also consist of stretchy elastomer material, such as, for example, silicone rubber, fluoroelastomer, polychloroprene, polyurethane or chlorosulfonated polyethylene. The protective membrane may also be treated with particular agents and thereby altering the properties of the protective membrane. The protective membrane may thus be coated with, for example, teflon (PTFE, polytetrafluoroethylene). It is particularly important to be able to select the protective material and the possible additional treatment in such a manner, that the result enables action according to the invention even with very strong or corrosive chemicals. The protective membrane may also be designed in such a manner that it enables the protection of the separate magnet units, for example in devices containing 8, 12 or 96 channels. The shape of the protective membrane may be that of a tube, of a plate or it can be irregularly designed. There are particularly many alternatives when using an elastomer protective membrane, because then the magnet inside and the ferromagnetic tube may also give a shape to the protective membrane.

A preferred alternative to the protective membrane is an even or plate-shaped protective membrane consisting of stretchy material. Such a protective membrane may be an individual stretchy membrane in a particular frame. The frame is intended for to facilitate the use of the protective membrane and to bring about properties suitable for stretching the membrane. Another alternative is a roll-like embodiment, whereupon the protective membrane may be changed by simply rolling new protective membrane from a roll. Also this alternative may include the use of a frame, a specific support or a prop in the case where the protective membrane is being stretched during the actual use. The use of such a protective membrane, consisting of one plate, is a recommended alternative when consumption of material is desired to be avoided in the isolation and washing events. The use of a protective membrane that has the shape of a plate is also economically more advantageous than the use of protective membranes of large size that have been prepared and designed with molding tools.

The use of a plate-like protective membrane in an automated device is a very simple and efficient alternative. When using a plate-like protective membrane, an initial stretching may be performed in the first stage by means of a ferromagnetic sleeve. At this stage the magnet is still inside the ferromagnetic sleeve and there is no magnetic field directed to the microparticles outside the protective membrane. At the same time as the protective membrane is further maintained stretched, the magnet may be brought out of the ferromagnetic sleeve in an appropriate manner. Then the magnet stretches the protective membrane additionally and brings about a gathering of microparticles around the protective membrane at a spot, where the magnetic pole/poles are. By moving the magnet in or out of the sleeve, the solution in the tube is mixed by means of the magnet. Mixing can also be performed by moving the ferromagnetic sleeve up and down.

The embodiment presented above is particularly preferable when treating microparticles in small vessels, such as, for example, in microplates, that have, for example, 96, 384 or 1536 wells. The presented way of mixing the solution and the microparticles is preferred, because the whole device does not need to be moved. Mixing is brought about by solely moving the magnet and/or the ferromagnetic sleeve. The presented approach is particularly preferable for the reason, that no conventional shakers are needed in the process and the vessels may be simultaneously closed. Conventional shakers are not able to efficiently mix small amounts of solution and particularly not to keep the microparticles in solution. A great problem for the known devices and methods is the rapid sedimentation of the microparticles on the bottom of the well.

In the above mentioned known microplates, where small liquid volumes are used, the evaporation of the liquid during incubations and mixings is a critical issue. By using the protective membrane in the presented manner according to the invention, the microparticles may also be treated in small volumes, because the protective membrane closes the opening of the well at the same time, whereby the evaporation of the liquid decreases. Therefore no separate lid consisting of aluminum, rubber or gummed tape is according to the invention needed to cover the microplates during mixings and incubations.

Particularly when separate protective membranes are used in the transfer devices, the protective membrane may be designed in a specific manner in its tip. The design of the tip may be intended to bring about the transfer of an amount as large as possible of microparticles in a reliable manner, for example, from a viscous biological sample to another vessel. While gathering large amounts of microparticles to the tip of the oblong protective membrane, as is the case when using a longitudinally magnetised permanent magnet, the outer layers of microparticles continuously risk to be liberated and stay in the solution. Also the turgor at the interface of the solution and the air is very strong and brings about a similar effect causing the microparticles to be liberated.

The protective membrane may indeed be designed in such a manner, that the microparticles stay attached as well as possible to the protective membrane while moving the transfer device despite of the emerging currents and despite of the penetration of the liquid surface and the effect of the surface tension on the liquid surface. Therefore various niches and protuberances can be made to the protective membrane, whereby a reliable transfer of the collected microparticles to another solution is brought about. Then the protective membrane may consist either of stretchy or inelastic material.

The protective membrane made of stretchy material may have a particular design, that assures the reliable collection and transfer of a large amount of microparticles from a vessel to another. For this purpose the edges of the protective membrane may have particular protuberances and niches, where the microparticles gather. Then it is preferable to use a transversely magnetised magnet by means of which microparticles can be collected over a broad area. By designing the protective membrane particular structures supporting microparticle masses are brought about. The design also influences the disturbing effects of liquid currents and liquid tension. When using stretchy material and spots of varying thickness, the protuberances and niches of the protective membrane are stretched in various ways. This phenomenon can be efficiently utilised both in releasing microparticles and particularly in bringing about an efficient mixing in the solution.

In the presented manner the protective membrane itself acts as an element that brings about mixing and is thereby a very efficient device for performing the mixing. Most preferably the design of the protective membrane varies in different spots of the protective membrane. When microparticles are desired to be collected from the solution, the magnet is moved downwards and the membrane is simultaneously stretched. While stretching the protective membrane, the specific design of its surface brings about the gathering of microparticles to the sheltered and supporting areas on the surface of the protective membrane. When the microparticles are desired to be removed from the protective membrane, the magnet is moved upwards into the ferromagnetic sleeve. In order to secure the release of the microparticles the ferromagnetic sleeve may simultaneously be moved downwards, whereupon the protective membrane is stretched, and then again upwards and repeating these movements in an appropriate manner. In one embodiment a specific mixing unit consists of a stretchy protective membrane and a movable bar inside the protective membrane. There does not need to be a magnet, but its function is to stretch and loosen the protective membrane from within in order to bring about an efficient mixing in the solution. Such a mixing unit may be used simultaneously to close the opening of the vessel.

A very efficient mixing is brought about in the liquid in the vessel at the same time, because the appropriate form of the surface of the protective membrane acts like an underwater wobble pump. Alternatively it is possible to move the magnet downwards and thereby stretch the protective membrane, when an efficient mixing is desired to be brought about based on the previously described phenomenon. Moving the magnet instead of the ferromagnetic tube simultaneously brings about also moving of the microparticles towards the magnet and the surface of the protective membrane, that further enhances the mixing. These previously mentioned methods for mixing a liquid may also be combined in an appropriate manner. This kind of a method for mixing works also when using a longitudinally magnetised magnet.

The ferromagnetic tube described in the invention may also be an individual tube, a set of several tubes together or an arrangement, where individual tubes form a specific formation of tubes. In one embodiment of the invention the ferromagnetic tube may be a specific ferromagnetic plate, that has one or several holes, where one or several magnets may move. Such an arrangement is particularly preferred when using small volumes, for example, 8-, 24-, 48-, 96- and 384-well plate formats, such as microplates and the like.

According to the invention there may also be an approach, which includes a separate magnet unit for collecting microparticles and a specific device or bar for moving the liquid surface in an appropriate manner described in the invention. This approach enables solutions, where the magnetic bars do not move at all, but the moving of the liquid and the microparticles is seen to by means of an organ particularly designed for this purpose. The vessel used in such an approach or the reactor is designed in an appropriate manner to meet the needs described herein.

In one embodiment according to the invention there are several separate magnet units, which all include their own protective membrane. These magnet units may be grouped in an appropriate formation, such as, for example, fan-like in line, along the arc of a circle or several arcs of a circle within each other, whereby each bar gather an appropriate amount of particles around it.

The device and the method according to the invention are not limited to, for example, molecular biology or purification of proteins, but they are generally applicable in fields, where ligands bound to microparticles can be used to synthesize, bind, isolate, purify or enrich desired biological components from various samples: diagnostic applications, biomedicine, enrichment of pathogens, synthesis of chemicals, isolation of poisons, viruses, bacteria, yeasts and cells. Also analytical methods, immunoassays and DNA hybridisation methods are within the scope of the invention.

Method Application of the Invention

The device and the method according to the invention are applicable to be used in very many application areas, for example, protein chemistry, molecular biology, microbiology, cell biology and proteomics. The invention has applications in the industry, diagnostics, analytics and research.

For purifying proteins there is a need for purification experiments in small volumes and, on the other hand, to increase the capacity to even very large volumes. By means of the described invention protein purifications may be done, when the need arises, from various sample volumes. Protein chemists need to be able to purify protein from a sample that has been pre-treated as little as possible, such as, for example, cell lysates. It is also important to change the capacity of purification according to ever changing needs. At present it is possible by changing the column sizes to be used. As the purification proceeds, enrichment of the protein is-one of the essential operations. In practice this means decreasing the liquid volume without any significant loss or denaturation of proteins. At present the most widely used methods include dialysis or filtration. Both of these methods require a lot of time. By means of the device and the method described in this invention a versatile method, that is applicable for varying sample volumes, can be provided to the field of proteins. Changing the capacity is easy without buying or preparing new columns. For a larger sample volume a larger amount of microparticles is simply chosen and after the protein has been bound, microparticles and protein are collected out of the solution by means of the device and the method described in the invention. The washing steps can be performed either in the same vessel or by changing the vessel. In the previous case the washing buffers used need to be conducted out of the vessel and replaced with a fresh washing buffer. Changing the buffer may also be done by means of various valve or aspiration arrangements. After the washes the proteins bound to the microparticles may be released to a small volume and the protein solution may be efficiently enriched.

When the need arises, decreasing the volume can be performed in stages towards a smaller volume.

By means of the device and the method described in the invention, for example, ion exchange chromatography, reverse phase chromatography, hydrophobic chromatography and affinity chromatographic purifications can be made. Also gel filtration can be accomplished with the described device, but it requires performing the gel filtration in a column and thereafter collecting the microparticles by means of a device according to the invention and outflow of the proteins to a small volume. The method enables, for example, removing salt from samples without largely increasing the volume compared to classical gel filtration columns.

The use of immobilised enzymes to process various proteins, sugars, fats and various so called biopolymers is a very important application area for the described invention. An important characteristic compared to the use of soluble enzymes is the possibility to easily reuse the immobilised enzymes. Washing the immobilised enzyme by means of the described invention for further use is very easy and efficient.

Examples for essential groups of enzymes and individual enzymes, used for example in the industry, include:
CARBOHYDRASES: Alpha-Amylases, Beta-Amylase, Cellulase, Dextranase, Alpha-Glucosidase, Alpha-Galactosidase, Glucoamylase, Hemicellulase, Pentosanase, Xylanase, Invertase, Lactase, Pectinase, Pullulanase PROTEASES: Acid Protease, Alkaline Protease, Bromelain, Ficin, Neutral Proteases, Papain, Pepsin, Peptidases, Rennin, Chymosin, Subtilisin, Thermolysin, Trypsin LIPASES AND ESTERASES: Triglyceridases, Phospholipases, Esterases, Acetylcholinesterase, Phosphatases, Phytase, Amidases, Aminoacylase, Glutaminase, Lysozyme, Penicillin Acylase ISOMERASES: Glucose Isomerase, epimerases, racemases OXIDOREDUCTASES: Amino Acid Oxidase, Catalase, Chloroperoxidase, Glucose Oxidase, Hydroxysteroid Dehydrogenase, Alcohol dehydrogenase, Aldehyde dehydrogenase, Peroxidases LYASES: Acetolactate Decarboxylase, Aspartic Beta-Decarboxylase, Fumarase, Histidase, DOPA decarboxylase TRANSFERASES: Cyclodextrin Glycosyltransferase, Methyltransferase, Transaminase, Kinases

LIGASES

PHOSPHATASES: Alkaline Phosphatase

The use of enzymes is very common in many branches of the industry, some examples of which follow: the synthesis and modification of lipids, proteins, peptides, steroids, sugars, amino acids, medicines, plastics, fragrances, chemicals and so called chiral chemicals.

Various synthesizing and cleaving enzymes associated to glycobiology, such as, for example, endo- and exo-glycosidases, are also within the scope of the invention. Enzymes familiar from applications of molecular biology, such as restriction enzymes, nucleases, ribozymes, polymerases, ligases, reverse transcriptases, kinases and phosphatases are also within the scope of the method described in the invention. As examples of DNA/RNA modifying enzymes the following can be mentioned: CIAP (Calf Intestinal Alkaline Phosphatase), *E. Coli* alkaline phosphatase, exonucleases (for example, P1 nuclease, S1 nuclease), ribonucleases, RNases (e.g. Pancreatic RNase, RNase H, RNase T1, RNase M, RNase T2), DNA ligases, RNA ligases, DNA polymerases, Klenow enzyme, RNA polymerases, DNA kinases, RNA kinases, terminal transferases, AMV reverse transcriptase and phosphodiesterases. The use of these and other DNA/RNA modifying enzymes is very polymorphous both in the research and applications of molecular biology. Proteases are very important enzymes in proteomics and protein chemistry, example of which include trypsin[[ ]], chymotrypsin[[ ]], papain, pepsin, collagenase, dipeptidyl peptidase IV and various endoproteinases. Synthetic enzymes, catalytic antibodies and multi-enzyme complexes may be used in the ways described in the invention. The use of the invention is neither limited by the use of enzymes and other catalytic components in water-free conditions, for example in organic solvents.

As concrete examples of embodiments of the invention in the field of molecular biology the following may be mentioned:

Cloning of the DNA Inserts:

For cloning the DNA inserts restriction enzymes are needed, (e.g. EcoR I, Hind III, Bam HI, Pst I, Sal I, Bgl II, Kpn I, Xba I, Sac I, Xho I, Hae III, Pvu II, Not I, Sst I, Bgl I), creating blunt ends (e.g. heat stable polymerases, Klenow Fragment DNA Polymerase I, Mung Bean nuclease), ligations (e.g. T4 DNA Ligase, *E. coli* DNA Ligase, T4 RNA Ligase), phosphorylation (e.g. T4 Polynucleotide Kinase), dephosphorylation (e.g. CIAP, *E. coli* Alkaline Phosphatase, T4 Polynucleotide Kinase) and deletions (e.g. T4 DNA Polymerase, heat stable polymerases, Exo III Nuclease, Mung Bean Nuclease).

Synthesis and Cloning of the cDNA:

Reverse Transcriptase, RNase H, DNA polymerase I, T4 DNA polymerase I, *E. coli* DNA Ligase.

Labeling of Nucleic Acids:

5' labelling (e.g. T4 Polynucleotide Kinase), 3' addition (e.g. T4 RNA Ligase), 3' fill-in (e.g. Klenow Fragment DNA Polymerase I, T4 DNA Polymerase), 3' exchange (e.g. T4 DNA Polymerase, heat stable polymerases), nick translation (e.g. *E. coli* DNA Polymerase I, heat stable polymerases), replacement synthesis (e.g. T4 DNA Polymerase, heat stable polymerases, Exo III Nuclease), random priming (e.g. Klenow Fragment DNA Polymerase I, heat stable polymerases) and RNA probes (e.g. T7 RNA Polymerase, SP6 RNA Polymerase).

Sequencing of Nucleic Acids:

Sequencing of DNA (e.g. *E. coli* DNA Polymerase I, Klenow Fragment DNA Polymerase I, heat stable polymerases) and Sequencing of RNA (e.g. Reverse Transcriptase, heat stable Reverse Transcriptases).

Mutagenisation of Nucleic Acids:

Oligonucleotide directed (e.g. T4 DNA Polymerase, T7 DNA Polymerase, heat stable polymerases) and Misincorporation (e.g. Exo III Nuclease, Klenow Fragment DNA Polymerase I, heat stable polymerases).

Mapping:

Restriction (e.g. Exo III Nuclease), Footprinting (e.g. Exo III Nuclease) and Transcript (e.g. Reverse Transcriptase, Mung Bean Nuclease).

Purification of Nucleic Acids:

Isolation and purification of genomic DNA, PCR fragments, DNA/RNA probes and plasmid DNA.

DNA Diagnostic Techniques:

DNA Mapping, sequencing of DNA, SNP analyses (Single Nucleotide Polymorphism), chromosome analyses, DNA libraries, PCR (Polymerase Chain Reaction), Inverse PCR, LCR (Ligase Chain Reaction), NASBA (Nucleic Acid Strand-Based Amplification), Q beta replicase, Ribonuclease Protection Assay.

DNA Diagnostics:

RFLP (Restriction Fragment Length Polymorphism), AFLP (Amplified Fragment Polymorphism), diagnostics of bacterial infections, bacterial resistance for antibiotics, DNA fingerprints, SAGE (Serial Analysis of Gene Expression) and sequencing of DNA.

The method described for culturing and isolating cells may be broadly utilised. Cells of interest include, for example, stem cells, B lymphocytes, T lymphocytes, endothelial cells, granulocytes, Langerhans cells, leucocytes, monocytes, macrophages, myeloid cells, natural killer cells, reticulocytes, trophoblasts, cancer cells, transfected cells and hybridoma cells. Commonly known methods, such as, for example, a direct or indirect isolation method, may be used in isolation of cells. In the first one, the direct isolation method, the desired cells are separated by binding them to the surface of microparticles by utilising, for example, specific antibodies. In the indirect method, not the desired cells, but all the other cells are bound to the microparticles. The desired cells stay in this case in the solution.

The method described in the invention applies well to the culture, isolation, purification and/or enrichment of bacteria, viruses, yeasts and many other uni- or multi-cellular organisms. A particularly important application area is the enrichment of pathogenic bacteria, such as, for example, *Salmonella, Listeria, Campylobacter, E. Coli* O157 and *Clostridium*, viruses, parasites, protozoans or other small organisms from a large liquid volume. The device and the method described in the invention can be exploited also within these application areas.

Biocatalysis commonly refers to the use of bacteria, enzymes or other components containing enzymes in the process. Enzymes or bacteria can be immobilised to a suitable solid carrier and the agent being treated is brought into connection with the immobilised components by using, for example, classical columns. According to this invention cells or enzymes can be attached to microparticles in an appropriate manner, which microparticles may then be used according to the invention to perform various enzymatic reactions.

Also analytical methods, immunoassays and DNA hybridisation methods as examples for research and routine tests are within the scope of the invention.

Isolation of cell organelles and various cell fractions is also within the scope of the application area of the invention. Cell organelles may be purified in a normal manner by utilising, for example, specific antibodies and various affinity ligands.

There are different needs to purify nucleic acids, starting from the purification of tiny amounts of DNA (Deoxyribonucleic Acid), RNA (Ribonucleic Acid) or mRNA (Messenger RNA) from large volumes of several liters. The method according to the invention can be used to isolate nucleic acids from both large and small sample volumes efficiently.

By means of the method a chain can be formed between culturing/growing, isolation and purification events according to various needs. The desired cells may, for example, first be isolated from the sample and purified. Thereafter, for example, the cell organelles can be isolated from the cells. The cell organelles are purified and the process may continue, for example, with purification of DNA or proteins. Microparticles equipped with various coatings and characteristics can be used in stages during the process. The last stage may be for example, enrichment of the purified product to the desired volume, amplification and detection of the product.

BRIEF DESCRIPTION OF THE DRAWINGS

FIG. 10-30 present the action of vessels containing filters, the mixing unit and the magnet unit while treating microparticles.

FIG. 31-40 present the action of a layer of microparticles, vessels containing filters and the magnet unit while treating microparticles.

FIG. 41-46 present the closing of vessels containing filters and the action of the magnet unit while treating microparticles.

FIG. 47-59 present the use of an external magnet and a ferromagnetic sleeve as such, together with the mixing unit and the magnet unit while treating microparticles.

FIG. 60-71 present the use of an external magnet and ferromagnetic sleeve together with the vessel, the mixing unit and the magnet unit while treating microparticles.

FIG. 72-82 present the use of an external magnet and ferromagnetic sleeve together with the vessel, the mixing unit and the magnet unit while treating microparticles.

FIG. 83-94 present various mixing units.

FIG. 97-104 present the use of a transversely magnetised magnet and a layer of microparticles in the case, where microparticles are not released during the process from the top of the protective membrane.

FIG. 105-112 present the use of a magnet, magnetised along its longitudinal axis, and a layer of microparticles in the case where microparticles are not released during the process from the top of the protective membrane.

DETAILED DESCRIPTION OF THE DRAWINGS

Figure 1:
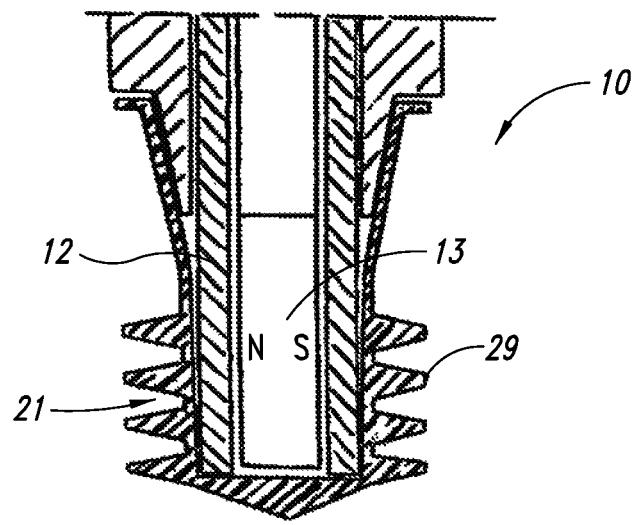
FIG. 1 presents a partially sectioned view of an embodiment of the magnet unit equipped with another kind of protective membrane.

FIG. 1 presents a magnet unit 10, that includes a transversely magnetised magnet 13, a ferromagnetic sleeve 12 and a protective membrane 21, that contains ridges 29 on its outer surface. Between the ridges 29 there are niches, where microparticles 22 gather and by means of which reliable collection of a large amount of microparticles to broad surfaces and their transfer from one vessel to another is assured.

Figure 2:
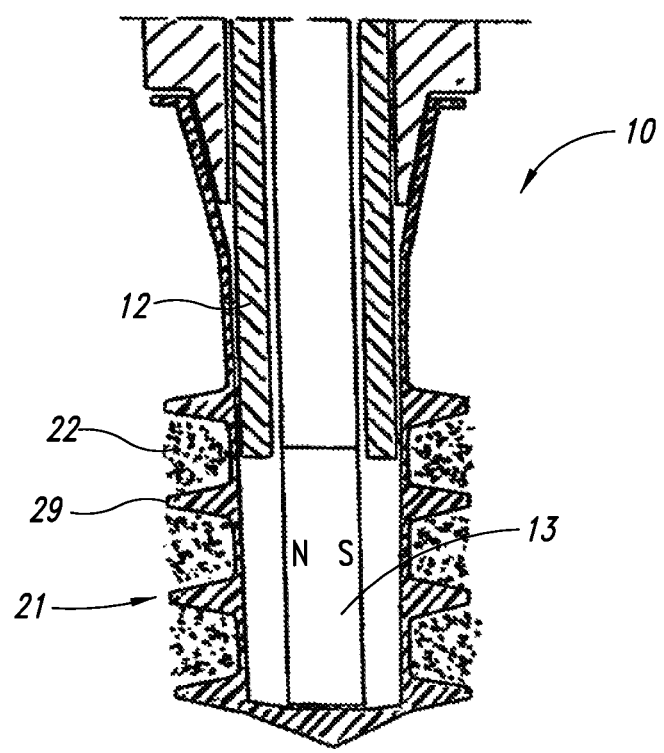
FIG. 2 corresponds to FIG. 1 and presents the action of the magnet unit in another stage.

FIG. 2 presents the magnet unit 10 of FIG. 17 in a position, where the magnet 13 is pushed completely out of the ferromagnetic sleeve 12. Then the transversely magnetised magnet 13 collects microparticles 22 to its protective membrane 21 with its whole length. When pushing the magnet 13 out, the protective membrane 21 thereby stretches in such as manner, that large niches or pockets will form between ridges 29. The microparticles 22 will stay in these pockets in such a manner, that it is easy to keep them still in place while lifting the magnet unit 10. The liquid currents caused by the movement of the magnet unit 10 and the disturbing effect of surface tension caused by penetration of the surface do not release microparticles 22 from the pockets.

Figure 3:
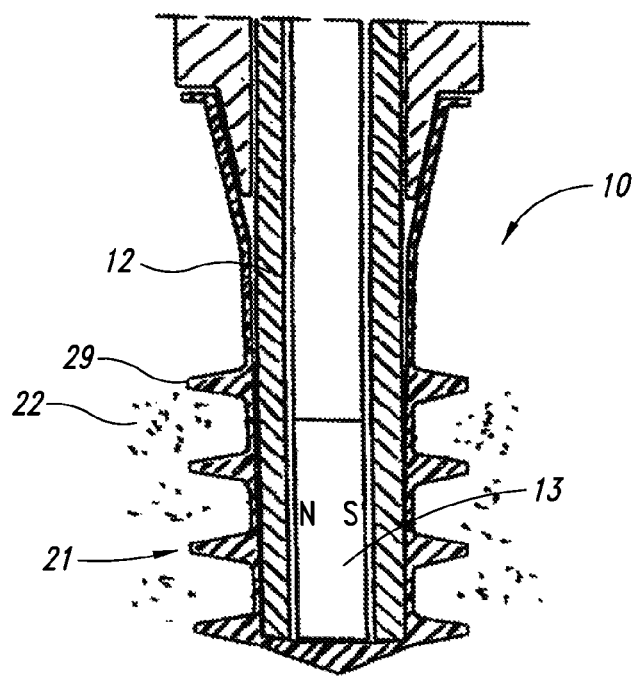
FIG. 3 corresponds to FIG. 1 and presents the action of the magnet unit in the third stage.

FIG. 3 presents a situation, where the magnet 13 is pushed completely out of the ferromagnetic sleeve 12 and simultaneously the ferromagnetic sleeve 12 is also pushed completely out. Then the ferromagnetic sleeve 12 pushed on top of the magnet 13 neutralises the magnetic force of the magnet 13 and the microparticles 22 are released from the protective membrane and transferred to the liquid.

Figure 4:
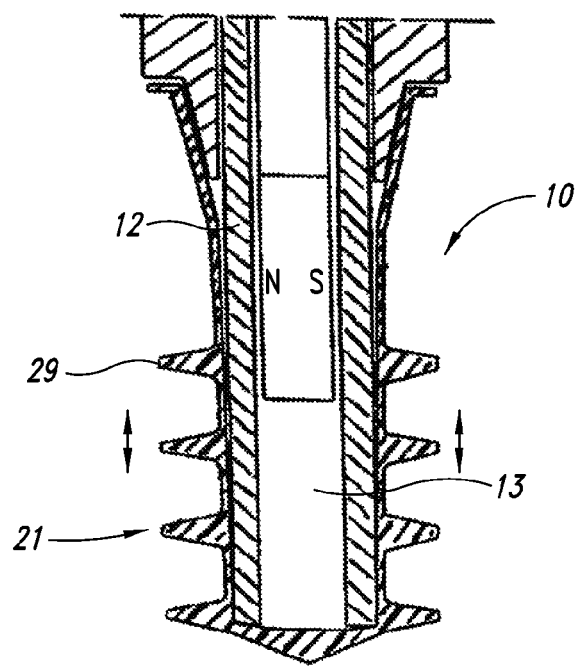
FIG. 4 corresponds to FIG. 1 and presents the action of the magnet unit in the fourth stage.

FIG. 4 again presents a situation, where only the ferromagnetic sleeve 12 is completely pushed out. In this case the magnet 13 does neither have magnetic force, and so the microparticles 22 do not gather on the surface of the protective membrane 21. This stage presented in FIG. 26 can instead be used by turns with the stage in FIG. 23, whereby an efficiently mixing pump effect is brought about in the liquid. Also the stages in FIGS. 18 and 19 can naturally be used by turns, that is, while the magnet 13 is completely pushed out, only the ferromagnetic sleeve 12 is moved back and forth. A mixing pump effect is achieved also in this manner in the liquid.

Figure 5:
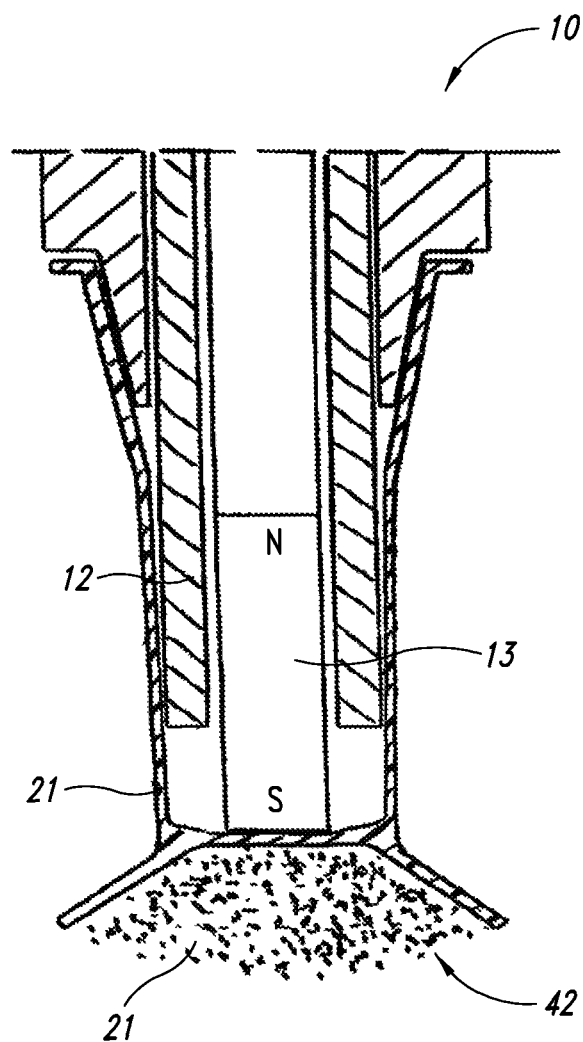
FIG. 5 presents a partially sectioned view of yet another embodiment of the magnet unit equipped with another kind of a protective membrane.

FIG. 5 presents another magnet unit 10, that includes a longitudinally magnetised magnet 13, a ferromagnetic sleeve 12 and a protective membrane 21, that has a pocket 42 at its end for microparticles 22. By means of such a structure a large amount of particles 22 may be collected, which particles do not easily get released from the surface of the protective membrane 21 during the transfer.

Figure 6:
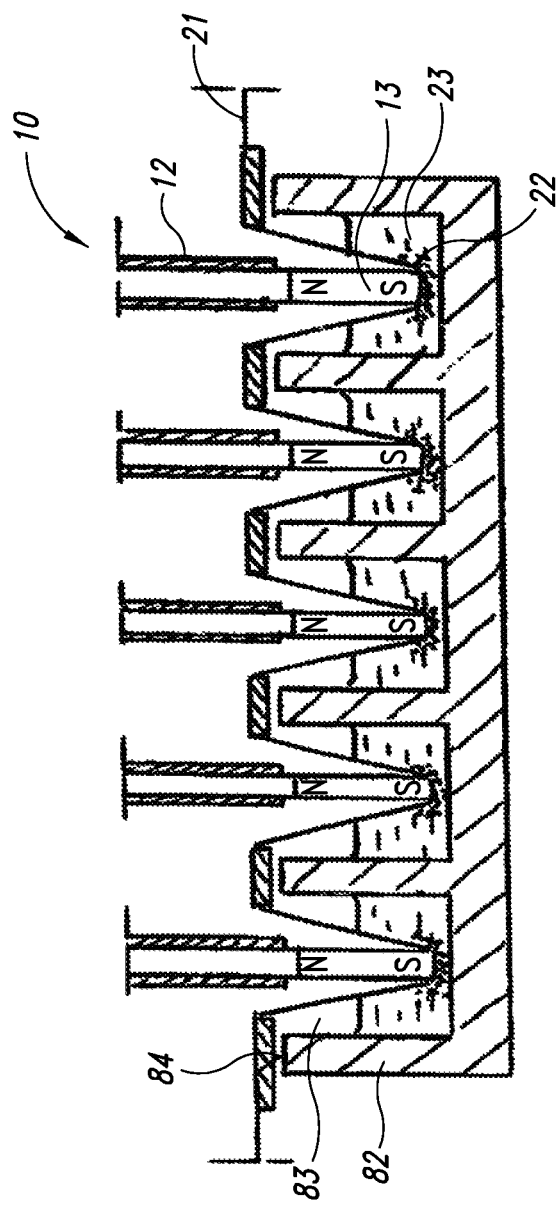
FIG. 6 presents schematically a sectioned view of several parallel magnet units, that have a mutual plate-like protective membrane.

FIG. 6 presents a vertical section of a microplate 82, which has several wells 83. There are several parallel magnet units 10 on top of the microplate 82, that have a common plate-like protective membrane 21. The protective membrane 21 consists of stretchy material, whereby the same membrane may be used jointly for the adjacent magnet units 10. The membrane is most preferably taken from a roll, whereupon it also is easily changeable.

Figure 7:
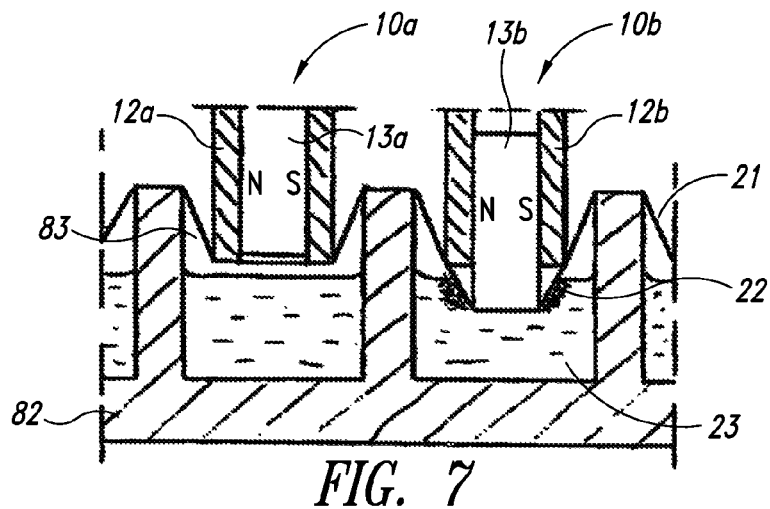
FIG. 7 corresponds to FIG. 6 and presents parallel magnet units according to a second embodiment.

FIG. 7 presents two parallel magnet units 10a and 10b, that have a common protective membrane 21. In the exemplary device of FIG. 7 the action of the magnet units 10a and 10b is at different stages. The ferrometallic sleeves 12a and 12b of both the magnet units 10a and 10b are pressed against the protective membrane 21 in such a manner, that the protective membrane 21 is pressed against the edges 84 of the wells 83 of the microplate 82 thereby closing and sealing the wells 83 with the membrane 21. The magnet of the magnet unit 10b is additionally pushed downwards-towards the well 83 of the microplate 82 in such a manner, that the protective membrane 21 and the head of the magnet 13b inside of it are in the liquid 23. Then the microparticles 22 in the liquid 23 gather in the end of the transversely magnetised magnet 13b on top of the protective membrane 21.

Figure 8:
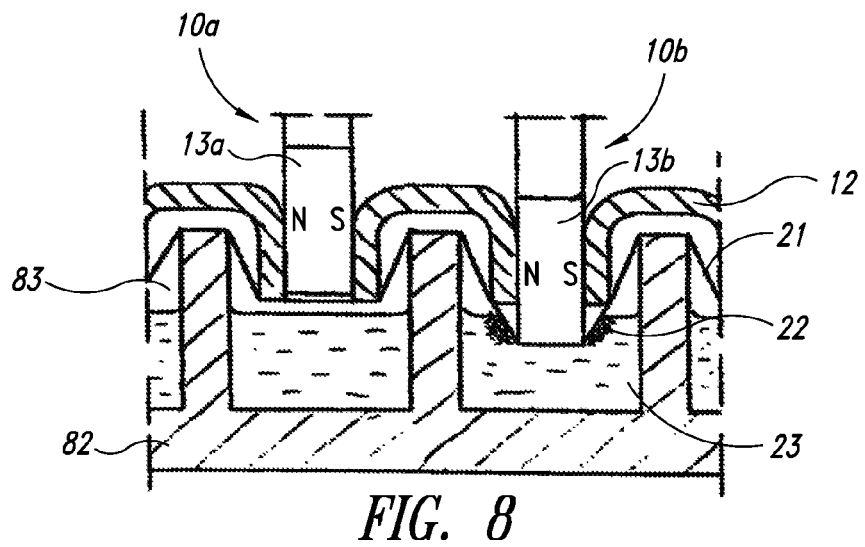
FIG. 8 corresponds to FIG. 6 and presents parallel magnet units according to a third embodiment.

FIG. 8 presents an embodiment, where the magnet units 10a and 10b do not contain separate ferrometallic sleeves. They are replaced by a ferrometallic plate 12, which is designed in such a manner, that there are juts projecting downwards right by the wells of the microplate. Magnets 13a and 13b are placed in the openings right by the juts of the ferrometallic plate 12. In FIG. 8 the action of the magnets 13a and 13b of the magnet units 10a and 10b are at different stages in the same way as in FIG. 7.

Figure 9:
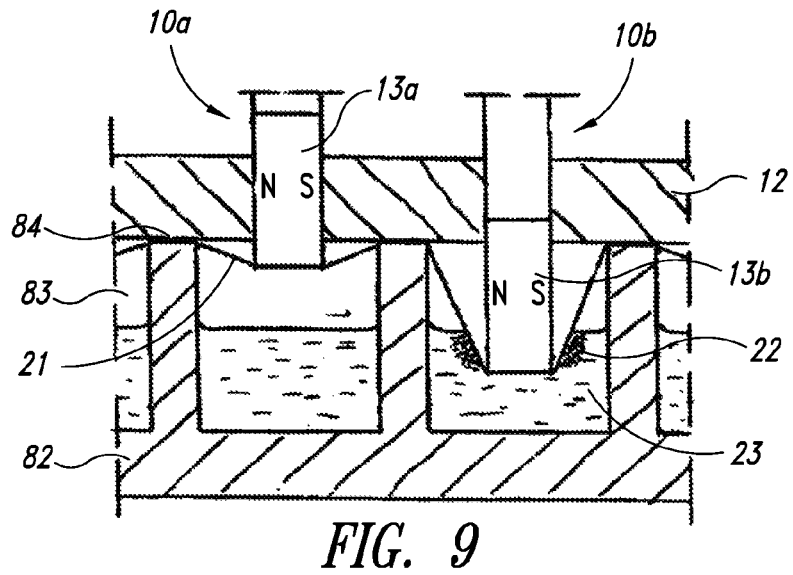
FIG. 9 corresponds to FIG. 6 and presents parallel magnet units according to a fourth embodiment.

FIG. 9 presents an embodiment, where the magnet units 10a and 10b also have a common ferrometallic plate 12 replacing the sleeves, which plate in this case is a straight plate. Magnets 13a and 13b are placed in the openings of the ferrometallic plate 12. Also in this figure the magnets 13a and 13b of the magnet units 10a and 10b are at different stages. As distinct from the solution in FIG. 7, the protective membrane 21 is pressed against the edges 84 of the wells 83 of the microplate 82 by means of magnets 13a and 13b and not by means of ferrometallic sleeves. The magnet 13a of the magnet unit 10a is in the sealing position, while the magnet 13b of the other magnet unit 10b is in the position for collecting microparticles.

FIG. 10-26 present stepwise a solution according to one embodiment, whereby the microparticles 22 in the vessel 26 are fetched by means of the magnet unit 10, that contains a protective membrane 21 consisting of elastomer material, such as, for example, silicone rubber. FIG. 10 presents a vessel 26, that contains appropriate microparticles 22 in a solution 23, which solution 23 and microparticles 22 may have been incubated appropriately in order to bind the desired biological components from the sample in the solution 23.

FIG. 11 presents a magnet unit 10, inside of which there is a transversely magnetised magnet 13 and the magnet 13 may be moved in the ferromagnetic sleeve 12. Such a magnet unit is brought into a vessel 26 and the microparticles 22 gather on the surface of the protective membrane 21 at the very spot, where the magnet 13 is outside the ferromagnetic sleeve 12.

The protective membrane 21 may also have ridges 29, between of which the microparticles 22 may very well settle down. The protective membrane 21 is stretched by means of the magnet 13, whereupon the distance between the ridges 29 in the protective membrane is also increased and more area for collecting is available.

FIG. 12 presents a situation, where the microparticles 22 collected to the magnet unit 10 may be transferred away from the solution 23 by removing the magnet unit 10 away from the vessel 26.

In FIG. 13 the magnet unit 10 is brought into a vessel 76 including a filter, which vessel contains appropriate liquid 23, such as, for example, appropriate wash buffers. The filter 77 may consist of various materials and it may have various thicknesses and the porosity grade may greatly vary according to different needs. In place of the filter 77 there may be a membrane or a specific solution including valves. In the vessel 76 including a filter, the magnet 13 of the magnet unit 10 is brought upwards inside the ferromagnetic sleeve 12, whereupon there is no magnetic field left around the protective membrane 21 and the microparticles 22 may be released from the surface of the protective membrane 21 into the solution 23.

In FIG. 14 the ferromagnetic sleeve 12 is used to stretch and loosen the protective membrane 21 appropriately in turns and thus currents are brought about inside the solution 23. It is possible by means of the method described in the invention to both efficiently mix the solution and further the release of the microparticles 22 from the surface of the protective membrane 21.

In FIG. 15 the microparticles 22 are collected from the vessel 76 including a filter by bringing the magnet 13 of the magnet unit 10 out of the ferromagnetic sleeve 12 and by stretching the elastomer protective membrane 21 in an appropriate manner. In FIG. 16 the magnet unit 10 is lifted from the vessel 76 including a filter. The backward-and-forward stretching of the protective membrane 21 brought about by means of the ferromagnetic sleeve 12 and the collecting of microparticles 22 by means of the magnet 13 may also be appropriately done in turns, in case very efficient mixing properties are desired to be brought about. In FIG. 17 the removing of the solution from the vessel 76 through the filter 77 on its bottom via the channel 85 joined to the bottom of the vessel 76 by means of an aspiration/vacuum unit, which unit is not presented in the figure, is presented.

In FIG. 18 appropriate new solution 23 is added to the vessel 76 containing the filter 77. If there is an appropriate space in the vessel 76, the magnet unit 10 does not need to be removed from the vessel 76 while adding the next solution 23. The magnet unit 10 can thereby be appropriately placed, for example, by one wall of the vessel 76 including a filter during the addition of the solution 23. In the next step a new solution 23 is added to the vessel including a filter.

In FIG. 19 the magnet unit 10 is brought back to the vessel 76 including a filter, to which vessel a new solution 23 is added. These buffer changes and collecting of microparticles may be performed with the vessel including a filter consecutively as many times as is desired. By means of an approach obtained in this manner the amount of disposables to be used may be greatly decreased, because multiple washes and incubations may be performed in the same vessel. FIG. 19 presents the release of microparticles 22 from the magnet unit 10 to the solution 23, as is described in FIG. 13.

In FIG. 20 the microparticles 22 are mixed by means of the magnet unit 10 in the solution 23 as previously described in FIG. 14. In FIG. 21 the magnet 13 of the magnet unit 10 is transferred outside the ferromagnetic sleeve 12 and the microparticles 22 are collected from the solution 23 on top of the protective membrane 21, as is described in FIG. 14. In FIG. 22 the magnet unit 10 and the microparticles 22 collected on top of the protective membrane 21 are transferred away from the vessel 76 including a filter. In FIG. 23 the magnet unit 10 is transferred to a new vessel 26. In FIG. 24 the microparticles 22 are released to the solution 23 in the manner presented in FIG. 14.

FIG. 25 presents a situation, where the magnet unit 10 is removed from the vessel 26 and the microparticles 22 released from the top of the protective membrane 21 are in the solution 23. The process may be continued from this vessel when the need arises. Finally the microparticles 22 may be totally removed from the vessel and the components bound on the surface of the microparticles 22 in the beginning of the process from the vessel 26 presented in FIG. 10 may be released to the solution.

FIG. 26 presents another way of proceeding from the situation described in FIG. 19. In FIG. 26 microparticles 22 are mixed in the solution 23 by means of the magnet unit 10 in the vessel 76 including a filter as is previously described in FIG. 14. In FIG. 27 the magnet unit 10 is transferred away from the vessel 76 including a filter and the microparticles 22 stay in the solution 23. FIG. 28 presents the aspiration of the solution 23 away from the vessel 76 containing the filter 77, for example, through the channel 85 joined to the bottom of the vessel by means of an aspiration or vacuum device. The microparticles 22 do not go along the solution, but stay on top of the filter 77. FIG. 29 presents the addition of the following solution to the vessel 76 including a filter.

FIG. 30 further presents the removal of the solution added in the previous figure in the manner described in FIG. 28. Finally the components bound to the microparticles 22 may be released and collected to a separate vessel placed in the vessel 76 containing the filter. All the removals done by means of the vessel 76 including a filter may be performed either by using a vacuum or a centrifuge. Additions of the solution 23 done to the vessel 76 including a filter may be performed by means of ordinary devices for liquid handling, such as manual pipettes or dispensers. Also automated devices for liquid handling may be applied in the method.

FIG. 31-40 present stepwise an approach according to one embodiment of the invention, whereby the microparticles 22 are in the vessel 76 containing the filter 77, in which vessel the removal of solutions and the addition of the following solution may be repeated many times. In FIG. 31 the microparticles 22 are in the solution 23 in the vessel 76 including a filter. In FIG. 32 the solution 23 is aspirated from the vessel 76 including a filter and the microparticles 22 stay on top of the filter 77 to form a layer of microparticles 78.

The following solution that may be, for example, a sample, is brought to the vessel 76 including a filter in FIG. 33. The solution may be further aspirated from the vessel 76, whereupon the desired components are bound on the surface of the microparticles 22 in the layer of microparticles 78. These steps may be repeated many times and finally an appropriate amount of solution 23 is added, which solution is not aspirated from the vessel 76 including a filter.

In FIG. 34 a magnetic tool 10 is brought into the vessel 76 including a filter. By moving the ferromagnetic sleeve 12 and the magnet 13 in an appropriate manner, the stretching and loosening of the protective membrane 21, and thereby an efficient mixing in the solution 23, is brought about. There may be appropriate ridges 29 on the surface of the protective membrane 21 in order to increase the efficiency of mixing and to further collecting of microparticles 22. By mixing the solution 23, the homogenisation of the layer of microparticles 78 on top of the filter 77 to the solution 23 is brought about. In FIG. 34 the protective membrane 21 is presented in its stretched form and in FIG. 35 the protective membrane 21 is presented in its non-stretched or shrunken form.

In FIG. 36 the transversely magnetised magnet 13 of the magnet unit 10 is brought out of the ferromagnetic sleeve 12 and the magnet 13 stretches the protective membrane 21 in an appropriate manner. The microparticles 22 from the solution 23 gather on top of the protective membrane 21. In FIG. 37 the magnet unit 10 is removed from the vessel 76 including a filter together with the collected microparticles 22 on top of the protective membrane 21. In FIG. 38 the magnetic tool 10 and the microparticles 22 are transferred to the new vessel 28, that contains the new solution 23.

In FIG. 39 the microparticles 22 are released from the surface of the protective membrane 21 by moving the ferromagnetic sleeve 12 on top of the magnet 13. The release of the microparticles 22 may be enhanced by appropriately stretching the protective membrane 21 by means of the ferromagnetic sleeve 12 or by moving the entire magnetic tool 10 in an appropriate manner.

In FIG. 40 the magnetic tool 10 is transferred away from the vessel 26 and the microparticles 22 are released to the solution 23. It is possible to proceed from this step forward and release, for example, the components bound from the original sample to the microparticles 21 to the solution 23. If the microparticles cause disturbance in the extended applications, the microparticles may be removed from the solution, if necessary. There may be various numbers of additions of the solution and/or the sample described previously to the vessel 76 including a filter. The number of treatments performed in the vessel 26 may also vary when the need arises. There may be various amounts of microparticles 22, whereupon their binding capacity may be greatly increased or decreased when the need arises. A particularly important application is to run a large volume of sample through the layer of microparticles 78, whereupon the desired sample is attached on the surface of the microparticles 22. There may be specific ligands, such as, for example, antibodies, peptides or nucleotides bound on the surface of the microparticles 22. There may be a biological component, such as, for example, bacteria, viruses, cells, nucleic acids, protein or peptide in the sample, which component is desired to be collected on the surface of the microparticles 22. The components bound on the surface of the microparticles 22 may finally be released to a small volume. This is particularly applicable to the case where there is very little of the component to be collected, such as bacteria, in a great volume of sample.

After treatment and possible washes, the microparticles are collected from the filter by means of the magnet unit. There may preferably be a transversely magnetised magnet in the magnet unit and an appropriately designed protective membrane, that together enable the collecting of even great masses of microparticles from the filter. By stretching the elastomer protective material according to the invention, a mixing of the solution is brought about, whereupon the microparticles gathered on the filter may be well liberated from the filter. By means of the magnet unit the microparticles may be further transferred to other vessels for possible further washing, incubating, eluating, amplifying and/or detecting.

The invention is not limited to the use of an elastomer protective membrane and a transversely magnetised magnet, but to the use of a magnetic tool in general together with a vessel including a filter according to the method. There does not need to be any separate protective membrane on top of the magnet.

FIG. 41-46 present stepwise an approach according to one embodiment, in which approach the use of more than one magnet unit and vessels 76 including a filter for treating microparticles, such as mixing, collecting, releasing and transferring, closing and opening vessels as well as handling solutions, such as removing and adding solutions, is presented. The magnet units and the vessels containing filters may be, for example, arranged in a row of 8 or 12 units. A very convenient application method may also be 24-, 48-, 96- and 384-well plates, whereupon the treatment of samples is remarkably faster.

Such an approach to treat microparticles is particularly applicable to an automated device, that includes the necessary dispenser for handling liquids, a vacuum work station (e.g. 96 and a 384-well format) for vessels containing filters and a multimagnet magnetic unit (for example, containing 8, 12 or 96 magnets).

FIG. 41 presents the closing of the vessel 76 including a filter by means of magnet units 10a and 10b by moving the magnet unit 10 and the microparticles 22 to the vessel 76 including a filter. In FIG. 42 the microparticles 22 are released from the top of the protective membrane 21 to the solution 23 by moving the magnet 13 into the ferromagnetic sleeve 12. In FIG. 43 the protective membrane is stretched by moving the ferromagnetic sleeve 12 and thus an efficient mixing is brought about in the solution. An important property is that the magnet unit 10 does not move entirely, but only the stretching movement of the protective membrane 21 in the solution is brought about by means of the ferromagnetic sleeve 12. The protective membrane 21 seals the vessel simultaneously with the mixing of the solution. In FIG. 44 the magnet 13 of the magnet unit 10 is moved outside the ferromagnetic sleeve 12 and it stretches the protective membrane 21. The microparticles 22 gather from the solution 23 on top of the protective membrane 21. In FIG. 45 the magnet unit 10 and the microparticles 22 are removed from the vessel 76 including a filter and the solution is also aspirated from the vessel. In FIG. 46 the following solution is added to the vessel 76 including a filter and the process may continue according to FIG. 41-45.

The protective membrane of the magnet unit 10 may have a specific design to increase the tightness of the junction between the protective membrane 21 in the magnet unit 10 and the vessel 76 including a filter. The simplest way to tighten the junction is to press the magnet unit 10 tightly against the vessel 76 including a filter. The stretching properties of the elastomer material in the protective membrane 21 may be utilised to close the vessel tightly and to open it easily. Solutions 23 may be changed several times when the need arises by simply aspirating the previous solution through a filter before adding a new one to the vessel.

FIG. 47-59 present stepwise an approach according to one embodiment, in which approach FIG. 47 presents a vessel 26 containing microparticles 22. The microparticles 22 may be coated with an appropriate ligand and there may be an appropriate sample in the solution 23, of which sample a given biological component is desired to be bound on the surface of the microparticles 22. In FIG. 48 the vessel 26 is moved beside the magnet 13 outside the vessel 26, whereupon the microparticles 22 gather to form a layer of microparticles 78 in the vicinity of the magnet 13 on the inner surface of the vessel. FIG. 49 presents a situation, where the solution 23 is aspirated from the vessel 26 in such a manner, that the microparticles 20 stay on the surface of the vessel 26. In FIG. 50 the following solution 23 is added to the vessel 26 and the magnetic field is removed by moving the ferromagnetic sleeve 12 on top of the magnet 13. When the magnetic field is absent, the microparticles 22 may be brought to a homogenised state in the solution 23 by mixing the solution 23 in different ways.

In FIG. 51 the microparticles 22 are homogenised from the layer of microparticles 78 to the solution 23, for example, by means of the tip of a pipette by moving the solution 23 back and forth in the vicinity of the layer of microparticles 78. In FIG. 52 the ferromagnetic sleeve 12 is removed from around the magnet 13, whereupon the magnetic field draws the magnetic particles to form a pellet. Thereafter the solution 23 is aspirated and the following solution is added. These intermediate steps may be repeated when the need arises depending on the application. Compared to the conventional method, this method does not require moving the vessel or the magnet physically far away from each other.

In FIG. 53 the magnetic tool 10 described in the invention is brought to the solution 23 in the vessel 26 and the protective membrane 21 is stretched downwards by means of the ferromagnetic sleeve 12. In FIG. 54 the ferromagnetic sleeve 12 is moved upwards and the stretching of the protective membrane 21 is decreased in the solution 23. By repeatedly stretching and loosening the elastomer protective membrane 21 in such a manner, that the magnet 13 is not outside the ferromagnetic sleeve 12, a good mixing is obtained and the microparticles 22 are homogenised from the layer of microparticles 78 to the solution 23. Stretching the protective membrane 21 is performed by means of the ferromagnetic sleeve 12. At the same time as the solution 23 is being mixed by stretching the protective membrane 21, the vessel 26 may be tightly closed by means of the magnet unit 10 and the protective membrane 21 and thus the evaporation of the solutions from the vessel 26 may be inhibited. This embodiment is particularly preferred in the case, where long incubations and/or high temperatures are desired to be used, whereupon the evaporation becomes a considerable problem.

In FIG. 55 the microparticles 22 are collected by means of the magnet unit 10 on the top of the protective membrane 21 by moving the magnet 13 out of the ferromagnetic sleeve 12. In FIG. 56 the microparticles 22 are transferred together with the magnet unit 10 from the vessel 26. The solution 23 may be aspirated from the vessel 26 and the following solution and the microparticles 22 may be brought back to the same vessel 26. Another way is to transfer the microparticles 22 to another vessel, where the microparticles 22 may also be released when the need arises.

In FIG. 57 a specific mixing tool is brought to the vessel 26 and the protective membrane 21 is in its stretched form. The basic principle of the mixing tool 80 in relation to the mixing effect is the same as is presented in FIGS. 53 and 54, i.e. by stretching the elastomer protective membrane 21 back and forth, currents are brought about in the solution and simultaneously the opening of the vessel is closed. In this case there is no magnet in the mixing tool 80, but a specific bar 11 inside the protective membrane 21, by moving of which bar the protective membrane consisting of elastomer material may be stretched and loosened when the need arises.

FIG. 58 presents the mixing tool when the protective membrane is in its loosened form and a homogenised solution 23 of the microparticles 22 is obtained. In FIG. 59 the ferromagnetic sleeve 12 is removed from around the magnet 13 outside the vessel 26, whereupon the microparticles form a layer of microparticles 78 on the inner surface of the vessel. The mixing tool 80 is removed from the vessel 26 or it is in the vessel 26 even when the solution 23 is aspirated from the vessel 26 and the following solution is added to the vessel 26.

FIG. 60-71 present stepwise an approach according to one embodiment, in which approach treating a set of vessels containing filters, such as, e.g. a 96-format plate, and microparticles 22 together with the magnet unit 10 and the mixing tool 80. In FIG. 60 there is a magnet 13 under the set of vessels containing filters and between the separate vessels 76, around of which magnet there is the ferromagnetic sleeve 12 that may be moved in relation to the magnet 13. The microparticles 22 are in the solution 23 in the vessels 76 containing filters.

In FIG. 60 there is the ferromagnetic sleeve 12 on top of the magnet 13 and the magnetic field is switched off. In FIG. 61 the ferromagnetic sleeve 12 is moved from around the magnet 13, whereupon the magnetic field of the magnet 13 gathers the microparticles 22 to form a layer of microparticles 78 on the inner surface of the vessels 76. In FIG. 62 the solution 23 may be aspirated through the filter bottom 77, for example, by means of a vacuum device and the layer of microparticles 78 stays attached to the inner surface of the vessel 76 including a filter by means of the magnetic field of the magnet 13.

In FIG. 63 the following solution 23 may be added to the vessel 76 including a filter and the ferromagnetic sleeve 12 is again moved on top of the magnet 13. In FIG. 64 there is no longer a magnetic field projected to the layer of microparticles 78, but the layer of microparticles 78 can not be homogenised to the solution 23 without mixing. In an embodiment of the invention both the magnet 13 and the ferromagnetic sleeve 12 may be separately moved. Then the spot, where the microparticles 22 gather, and the area of this spot may be controlled simply by means of the magnet 13 and the ferromagnetic sleeve 12. FIG. 60-63 present an embodiment, where the magnet 13 does not move, but only the ferromagnetic sleeve 12 moves in relation to the magnet 13.

In FIG. 65 a specific mixing tool is brought into the vessel 76 including a filter, which tool has an elastomer protective membrane 21 and a bar 11, that may be moved up and down inside the protective membrane 21. By moving the bar 11 downwards, the protective membrane 21 is stretched and in FIG. 65 the protective membrane 21 is presented in its stretched form. In FIG. 66 the bar 11 is moved upwards and the tension of the protective membrane 21 is restored. By means of such a mixing, liquid currents are brought about in the solution 23 and the method is particularly well suited for mixing microparticles 22 in small volumes, such as, e.g. in 96-well plates. The mixing tool 80 itself does not move during this event, but only the bar 11 inside the protective membrane 21 is moving. In this case the mixing tool 80 and the protective membrane 21 in it may close the vessel 76 including a filter during the mixing. While the mixing tool 80 is mixing, the magnet outside the vessel 76 including a filter is completely covered with the ferromagnetic sleeve 12.

In FIG. 67 the ferromagnetic sleeve 12 is moved away from around the magnet 13 outside the vessel 76 including a filter and the microparticles 22 may be collected to form a layer of microparticles 78 on the inner surface of the vessel 76 including a filter. The mixing tool 80 is removed from the vessel 76 including a filter. After this step the solution 23 may be aspirated through the filter 77 and the following solution may be added to the vessel 76 including a filter. If the opening of the vessel 76 including a filter does not need to be closed during the mixing step, the protective membrane of the mixing tool 80 does not need to consist of elastomer material and it is possible that it does not need to be a protective membrane at all. In this case mixing is performed by means of a rod, a bar or a peg consisting of only plastic or other suitable material.

In FIG. 68 the magnet unit 10 is brought into the vessel 76 including a filter, on top of which unit there is a protective membrane 21, which is stretched to bring about mixing in the manner presented in FIGS. 65 and 66, in which case the magnet 13 is constantly inside the ferromagnetic sleeve 12. In FIG. 68 the protective membrane 21 is in its stretched form.

The ferromagnetic sleeve 12 acts as the factor stretching and loosening the protective membrane 21. Also in this case the magnet unit 10 and the protective membrane 21 may close the opening of the vessel 76 including a filter during mixing and other events. In FIG. 69 the protective membrane is in its loosened form and the microparticles 22 are homogenised in the solution 23.

In FIG. 70 the microparticles 22 are collected on the top of the protective membrane 21 by moving the magnet 13 out of the ferromagnetic sleeve 12 and by stretching the protective membrane 21 by means of the magnet 13. In FIG. 71 the magnet unit 10 and the microparticles 22 collected on top of the protective membrane 21 are removed from the vessel 76 including a filter. The solution 23 may be aspirated through the filter 77 and the following solution may be added to the vessel 76 including a filter. The microparticles 22 may be brought by means of the magnet unit 10 back into the vessel 76 including a filter and mixings and collectings described previously may be performed when the need arises. The microparticles 22 may also be brought to another vessel for further treating.

FIG. 72-82 present stepwise an approach according to an embodiment, in which approach treating a set of vessels containing filters, such as, e.g. a 8-, 24-, 48- or 96-well plate, and microparticles 22 together with the magnet unit 10 and the mixing tool 80 is presented. In FIG. 72 there is a magnet 13 under the set of vessels containing filters and between the separate vessels 76, around of which magnet there is the ferromagnetic sleeve 12 that may be moved in relation to the magnet 13. The microparticles 22 are in the solution 23 in the vessels 26. In FIG. 72 there is a ferromagnetic sleeve 12 on top of the magnet 13 and the magnetic field is switched off.

In FIG. 73 the ferromagnetic sleeve 12 is moved away from around the magnet 13, whereupon the magnetic field of the magnet 13 collects the microparticles 22 to the inner surface of the vessels 26 to form a layer of microparticles 78. In FIG. 74 the solution 23 may be aspirated, for example, by means of washers or pipettes and the layer of microparticles 78 stays attached to the inner surface of the vessels 26 by means of the magnetic field of the magnet 13. In FIG. 75 the following solution 23 may be added to the vessel 26 and the ferromagnetic sleeve 12 is moved again on top of the magnet 13. In an embodiment of the invention both the magnet 13 and the ferromagnetic sleeve 12 may be separately moved. Then the spot, where the microparticles 22 gather and the area of this spot may be controlled simply by means of the magnet 13 and the ferromagnetic sleeve 12. FIG. 72-75 present an embodiment, where the magnet 13 does not move, but only the ferromagnetic sleeve 12 moves in relation to the magnet 13.

In FIG. 76 a specific mixing tool is brought into the vessel 26, which tool has an elastomer protective membrane 21 and a bar 11, that may be moved up and down inside the protective membrane 21. By moving the bar 11 downwards the elastomer protective membrane 21 is stretched and in FIG. 76 the protective membrane 21 is presented in its stretched form. In FIG. 77 the bar 11 is moved upwards and the tension of the protective membrane 21 is restored. By means of such a mixing liquid currents are brought about in the solution 23 and the method is particularly well suited for mixing microparticles 22 in small volumes, such as, e.g. in 96- and 384- well plates. The mixing tool 80 itself does not move during this event, but only the bar 11 inside the protective membrane 21 is moving. In this case the mixing tool 80 and the protective membrane 21 in it may close the vessel 76 including a filter during the mixing. While the mixing tool 80 is mixing, the magnet outside the vessel 26 is completely covered with the ferromagnetic sleeve 12.

In FIG. 78 the ferromagnetic sleeve 12 is moved away from around the magnet 13 outside the vessel 26 and the microparticles 22 may be collected to form a layer of microparticles 78 on the inner surface of the vessel 26. The mixing tool 80 is removed from the vessel 26. After this step the solution 23 may be aspirated and the following solution may be added to the vessel 26. If the opening of the vessel 26 does not need to be closed during the mixing step, the protective membrane of the mixing tool 80 does not need to consist of elastomer material and it is possible that it does not need to have a protective membrane at all. In this case mixing is performed by means of a rod, a bar or a peg consisting of only plastic or other suitable material. The rods, bars and pegs used for mixing may be disposable and they may be, for example, in 96-format, if a 96-well plate is being mixed.

In FIG. 79 a magnet unit 10 is brought into the vessel 26, on top of which unit there is a protective membrane 21, which is stretched to bring about mixing in the manner presented in FIGS. 76 and 77, in which case the magnet 13 of the magnet unit 10 is constantly inside the ferromagnetic sleeve 12 of the magnetic tool 10. In FIG. 79 the protective membrane 21 is in its stretched form. The ferromagnetic sleeve 12 of the magnet unit 10 acts as the factor stretching and loosening the protective membrane 21. Also in this case the magnet unit 10 and the protective membrane 21 may close the opening of the vessel 26 during mixing and other events.

In FIG. 80 the protective membrane 21 is in its loosened form and the microparticles 22 are homogenised in the solution 23. In FIG. 81 the microparticles 22 are collected on the top of the protective membrane 21 by moving the magnet 13 of the magnet unit 10 out of the ferromagnetic sleeve 12 and by stretching the protective membrane 21 by means of the magnet 13. In FIG. 82 the magnet unit 10 and the microparticles 22 collected on top of the protective membrane 21 are removed from the vessel 26. The solution 23 may be aspirated and the following solution may be added to the vessel 26. The microparticles 22 may be brought by means of the magnet unit 10 back into the vessel 26 and mixings and collectings described previously may be performed when the need arises. The microparticles 22 may also be brought to another vessel for further treating.

FIG. 83-94 present stepwise an approach according to yet another embodiment. FIG. 83 presents a mixing tool 80, that has a protective membrane 21. The protective membrane 21 has different ridges 29 and the protective membrane 21 is in its stretched form in the solution 23. There is a bar 11 inside the protective membrane 21, which bar may be moved upwards and downwards. The bar 11 may consist of different materials (for example, plastic or metal). Currents may be brought about in the solution 23 when stretching the protective membrane 21 by pressing the bar 11 downwards and loosening the stretch by moving the bar 11 upwards. Currents may be further enhanced when using different ridges 29 on the surface of the protective membrane 21 and by choosing the vessel 26 appropriately.

In FIG. 84 protective membrane 21 is in its loosened form. In FIGS. 83 and 84 the opening of the vessel 26 is closed by means of the mixing tool 80 in order to decrease evaporation and minimise the risk for splashing. Closing the vessel 26 may be performed during the mixing, because only the bar 11 inside the mixing tool 80 is moving, thereby stretching the protective membrane 21 consisting of elastomer material. Such an approach is particularly efficient in automated devices and when mixing small volumes.

FIG. 85 presents an approach, where the protective membrane 21 is solid for adjacent mixing tools 80 and vessels 26 containing solution 23. The protective membrane 21 is stretched and loosened by means of the bar 11. In FIG. 85 the protective membrane 21 is in its loosened form and the protective membrane 21 solid for vessels 26 closes the opening of the vessels 26. In FIG. 86 the protective membrane 21 is in its stretched form and the bar 11 is pressed downwards. A particularly preferred embodiment is, for example, one solid protective membrane, for example, a plate consisting of silicone rubber on top of the microtiter plate, such as, for example, 96-, 384-, 1536-well plates. Also in this approach the closing of the wells may be arranged simultaneously while the solutions in the wells are being mixed. By means of such-an embodiment either all wells may be mixed or only desired wells may be mixed while the other wells may be left unmixed. A particularly preferred embodiment are reactions and incubations performed in high temperature, whereby evaporation is considerable. By closing the vessels tightly evaporation may be remarkably reduced.

FIG. 87-94 present different mixing tools as pairs, where the other one is in its stretched and the other one in its loosened form. The figures present different alternatives for the design of the protective membrane 21. An appropriate design of the protective membrane is also dependent on the inner measures and ridges of the vessel as well as the amount of solution to be used in the vessel.

Figures 95, 96:
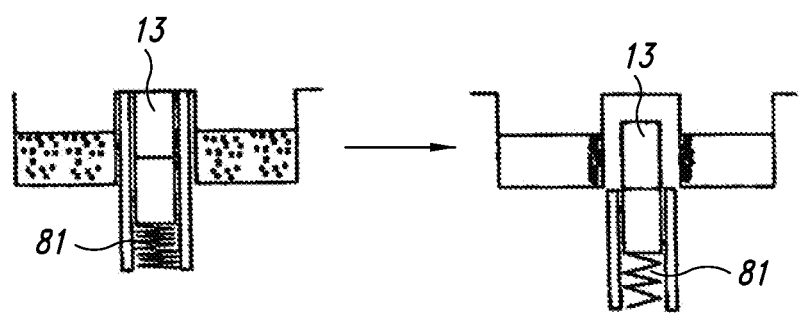
FIGS. 95 and 96 present the use of an external magnet, ferromagnetic sleeve and a spring under the magnet while treating microparticles.

FIGS. 95 and 96 present stepwise an approach according to an embodiment, where a possible approach is presented for the use of an external magnet and a ferromagnetic sleeve, for example, with 96-well plates. There is the transversely magnetised magnet 13 and the ferromagnetic sleeve 12 in FIG. 95. In addition there may be a spring suspension 81 under the magnet. By pressing the vessel 26, for example, a 96-well plate downwards, the vessel 26 simultaneously presses the magnet 13 inside the ferromagnetic sleeve 12 and the string 81 under the magnet 13 tightens. When the magnet 13 is inside the ferromagnetic sleeve 12, there is no magnetic field outside and the microparticles 22 stay in the homogenised solution 23.

In FIG. 96 the vessel 26 is no longer pressed down, but due to the string 81 the magnet 13 comes out of the ferromagnetic sleeve 12 and the magnetic force of the magnet 13 affects the adjacent vessels 26. The microparticles 22 in the vessels gather in the vicinity of the magnet 13 to form a layer of microparticles 76 on the inner surface of the vessel.

Pressing the vessel 26 may be performed, for example, by means of the magnet unit 10, described in the invention, or the mixing tool 80. The mixings described in the invention and the closing of the vessel 26 may be performed efficiently by means of such a string approach. By pressing the vessel 26 downwards, for example, by means of the magnet unit 10, the openings of the vessel are closed and simultaneously the external magnet 13 is pressed inside the ferromagnetic sleeve 12. When the vessel 26 is kept down by means of the magnet unit 10, the mixings described in the invention and the homogenisations, collections and transfers may be performed efficiently. Simultaneously the vessel 26 stays surely closed. The vessels 26 may also have filters on the bottom and the advantages described in the invention for using filter-bottom vessels crop out clearly also in this approach. The described string 81 does not need to be a string at all, but the movement of the magnet may be arranged by means of a specific motor, whereby the vessel is not needed at all for pressing the magnet 13 inside the ferromagnetic sleeve 12. The motorised version enables moving both the magnet and the vessel in use.

FIG. 97-112 present stepwise an approach according to yet another embodiment, in which the use of microparticles 22 on top of the protective membrane 21 of the magnet unit 10 throughout the whole process, such as, for example, when performing nucleic acid or protein purifications, immunoassays and DNA hybridisation assays. The microparticles 22 may be coated with appropriate ligands (for example, with antibodies, oligonucleotides and peptides) to bind desired biological components from the solution/sample. It is essential, that the microparticles 22 are collected in the beginning of the process on the surface of the magnet unit, as is described in FIGS. 97 and 105, and that the microparticles are not released in the various wash steps or incubation steps, depending on the application, of the process. By means of the described method a particular, active reaction surface may be established by collecting the microparticles 22 by means of the magnet 13 on the surface of the protective membrane 21. The microparticles are not lost during the wash steps and incubation steps, because the microparticles 22 are not released during the process. Finally a measurement may be performed either in the solution 23 or in the layer of microparticles 78.

FIG. 97 presents a vessel 76 including a filter, in which vessel there is solution 23 containing microparticles 22. In FIG. 98 the magnet unit 10 is brought into the solution 23 in the vessel 76 including a filter and the microparticles 22 are collected on the surface of the protective membrane 21 to form a particular layer of microparticles 78. The protective membrane 21 may consist of elastomer or non-elastomer material. The magnet 13 presented in the figure is transversely magnetised, the ferromagnetic sleeve 13 is not on top of the magnet 13. By using the transversely magnetised magnet 13 the microparticles 22 may be collected over a very large area around the protective membrane 21. Such an approach is particularly preferred, when a very large area for collecting and reaction kinetics are needed, for example, in sensitive immunoassays. The layer of microparticles 78 may be washed in the vessel 76 including a filter by aspirating and adding appropriate solutions to the vessel including a filter. The additions and aspirations of solutions in the vessel 76 including a filter may be performed, for example, by means of aspiration/vacuum devices and dispensers.

In FIG. 99 the magnet unit 10 is removed from the vessel 76 including a filter to another vessel 26 containing a new solution 23. The layer of microparticles 78 is not homogenized to the solution 23, but the magnet unit 10 may be appropriately moved in the solution 23. In the vessel 26 also particular incubations may be performed by letting the magnet unit 10 and the protective membrane 21 be in the solution 23. The magnet unit 10 and the protective membrane 21 may appropriately close the opening of the vessel 26 and prevent evaporation of the solution 23. In FIG. 100 the magnet unit 10 is removed from the vessel 26 and the layer of microparticles 78 is on top of the protective membrane 21.

FIG. 101 presents the removal of the solution 23 from the vessel 26, for example, by means of a washer or a pipette. In FIG. 102 the addition of a new solution to the same vessel 26 is described. In FIG. 103 the magnet unit 10 is transferred to the vessel 23 now containing a new solution 23. The layer of microparticles 78 is not homogenised to the solution 23, but the layer of microparticles 78 may be moved and let stand in the solution 23 for an appropriate period of time. In FIG. 104 the magnet unit 10 and the layer of microparticles 78 on top of the protective membrane 21 are removed from the vessel 26. The solutions may be changed in the described process as many times as needed and finally a measurement for determining the concentration of the isolated biological component may be performed in the solution 23 in the vessel 26. Alternatively, the concentration of the biological component may be determined in the layer of microparticles 78.

FIG. 105 presents a vessel 76 including a filter, in which vessel there is solution 23 containing microparticles 22. In FIG. 106 the magnet unit 10 is brought into the solution 23 in the vessel 76 including a filter and the microparticles 22 are collected on the surface of the protective membrane 21 to form a particular layer of microparticles 78. The protective membrane 21 may consist of elastomer or non-elastomer material. The magnet 13 presented in the figure is magnetised along the longitudinal axis of the magnet unit 10, the ferromagnetic sleeve 13 is not on top of the magnet 13. By using the magnet 13 magnetised along the longitudinal axis of the magnet unit 10 the microparticles 22 may be collected precisely around the tip of the protective membrane 21. Such an approach is particularly preferred, when handling very small volumes of solutions. The layer of microparticles 78 may be washed in the vessel 76 including a filter by aspirating and adding appropriate solutions to the vessel 76 including a filter. The additions and aspirations of solutions in the vessel 76 including a filter may be performed, for example, by means of aspiration/vacuum devices and dispensers.

In FIG. 107 the magnet unit 10 is removed from the vessel 76 including a filter to another vessel 26 containing a new solution 23. The layer of microparticles 78 is not homogenised to the solution 23, but the magnet unit 10 may be appropriately moved in the solution 23. In the vessel 26 also particular incubations may be performed by letting the magnet unit 10 and the protective membrane 21 be in the solution 23. The magnet unit 10 and the protective membrane 21 may appropriately close the opening of the vessel 26 and prevent evaporation of the solution 23. In FIG. 108 the magnet unit 10 is removed from the vessel 26 and the layer of microparticles 78 is on top of the protective membrane 21. FIG. 109 presents the removal of the solution 23 from the vessel 26, for example, by means of a washer or a pipette.

In FIG. 110 the addition of a new solution to the same vessel 26 is described. In FIG. 111 the magnet unit 10 is transferred to the vessel 23 now containing a new solution 23. The layer of microparticles 78 is not homogenised to the solution 23, but the layer of microparticles 78 may be moved and let stand in the solution 23 for an appropriate period of time. In FIG. 112 the magnet unit 10 and the layer of microparticles 78 on top of the protective membrane 21 are removed from the vessel 26. The solutions may be changed in the described process as many times as needed and finally a measurement for determining the concentration of the isolated biological component may be performed in the solution 23 in the vessel 26. Alternatively, the concentration of the biological component may be determined in the layer of microparticles 78.

According to the invention, one embodiment for the method presented in FIG. 97-112 is to use vessels containing all the necessary solutions, microparticles, antibodies, labels, wash buffers and substrates readily dispensed. Vessels containing the previously mentioned solutions may also be closed by means of aluminum foil, different stickers or elastomer solutions.

FIG. 97-112 present a way of producing and using the layer of microparticles as an expansive solid-phase, that is applicable also with different vessels, such as, for example, tubes and wells. Then by utilising an external magnet and a ferromagnetic sleeve the microparticles are bound to the inner surface of the vessel to form an appropriate layer. The magnet approach may also be of another kind, such as, an electric magnet or a regular permanent magnet. The layer of microparticles ought to be relatively thin, whereby the advantages described in the Invention are achieved. It is also possible to use mixing methods described in this invention with such a vessel and the closing of the opening of the vessel in the case, where the methods are desired to be efficiently exploited.

Transferring and using the magnet unit, even when it does not contain an elastomer protective membrane, together with vessels containing filters and an external magnet, are within the scope of the invention of the patent. The above mentioned embodiments of the invention serve only as examples of applying the idea according to the invention. It is evident for those skilled in the art that various embodiments may exist within the scope of the claims that follow farther behind.

LIST OF REFERENCE NUMERALS 10 magnet unit
11 bar
12 ferromagnetic tube or sleeve
13 magnet
21 protective membrane
22 microparticles
23 solution
25 liquid surface
26 vessel
28 rotational axis
29 ridge of the protective membrane
40 multi-channel transfer device for microparticles
41 group of magnet units
42 pocket
76 vessel including a filter on its bottom
77 filter
78 layer of microparticles
79 tip of a pipette or a dispenser/washer
80 mixing device
81 spring
82 microplate
83 well
84 edge of the well
85 outlet channel

The invention claimed is:

1. A device for handling magnetic microparticles that bind a desired component from a sample, comprising:
    (a) magnetic microparticles (22) selected from the group consisting of: ferromagnetic, paramagnetic or superparamagnetic particles, wherein the magnetic particles bind a desired component selected from the group consisting of: a nucleic acid, a protein, a peptide, a cell organelle, a bacterium, a cell, and a virus;
    (b) a vessel (26), wherein the vessel is a tube or a well; and
    (c) a magnetic tool (10), comprising a magnet (13), a protective shield (21) or coating, and a ferromagnetic sleeve (12), wherein the magnet (13) and the ferromagnetic sleeve (12) are each movable in relation to each other and wherein the magnetic field of the magnet (13) is increased when the magnet (13) is partly or completely outside the ferromagnetic sleeve (12).

2. The device according to claim 1, wherein the protective shield is an elastomer or non-elastomer shield (21) for binding the microparticles (22).

3. The device according to claim 1, wherein the protective shield is an elastomeric membrane covering the magnetic tool, wherein the elastic membrane has ridges on its outer surface.

4. The device according to claim 1, wherein the opening of the vessel (26) is closed by the magnetic tool (10).

5. The device according to claim 4, wherein the protective shield is an elastomeric membrane.

6. The device according to claim 1, comprising a filter (77) at the bottom of the vessel (26).

7. The device according to claim 6, wherein the bottom of the vessel (26) further comprises a channel (85) for conducting solution (23) through the filter (77) out from the vessel.

8. The device according to claim 1, wherein the magnet (13) has a magnetizing axis that is parallel to the longitudinal axis of the ferromagnetic sleeve (12) and the magnet (13).

9. The device according to claim 1, wherein the magnet (13) has a magnetizing axis that is transverse to the longitudinal axis of the ferromagnetic sleeve (12) and the magnet (13).

* * * * *